(12) United States Patent
Reb

(10) Patent No.: US 10,265,423 B2
(45) Date of Patent: Apr. 23, 2019

(54) RADIOPAQUE MONOMERS, POLYMERS, MICROSPHERES, AND METHODS RELATED THERETO

(71) Applicant: Biosphere Medical, Inc., South Jordan, UT (US)

(72) Inventor: Philippe Reb, Themericourt (FR)

(73) Assignee: Biosphere Medical, Inc., South Jordan, UT (US)

( * ) Notice: Subject to any disclaimer, the term of this patent is extended or adjusted under 35 U.S.C. 154(b) by 59 days.

(21) Appl. No.: 14/992,580

(22) Filed: Jan. 11, 2016

(65) Prior Publication Data

US 2016/0200670 A1     Jul. 14, 2016

Related U.S. Application Data

(60) Provisional application No. 62/102,384, filed on Jan. 12, 2015.

(51) Int. Cl.

| | |
|---|---|
| *C07C 237/04* | (2006.01) |
| *A61K 49/18* | (2006.01) |
| *A61K 31/704* | (2006.01) |
| *A61K 49/04* | (2006.01) |
| *C08F 220/58* | (2006.01) |
| *A61K 49/12* | (2006.01) |
| *A61K 9/00* | (2006.01) |
| *A61K 47/02* | (2006.01) |
| *A61K 9/16* | (2006.01) |
| *C07C 231/08* | (2006.01) |
| *C08F 222/38* | (2006.01) |

(52) U.S. Cl.
CPC ........ *A61K 49/1818* (2013.01); *A61K 9/0019* (2013.01); *A61K 9/1635* (2013.01); *A61K 31/704* (2013.01); *A61K 47/02* (2013.01); *A61K 49/048* (2013.01); *A61K 49/0438* (2013.01); *A61K 49/0442* (2013.01); *A61K 49/126* (2013.01); *C07C 231/08* (2013.01); *C08F 220/58* (2013.01); *C08F 222/385* (2013.01)

(58) Field of Classification Search
None
See application file for complete search history.

(56) References Cited

U.S. PATENT DOCUMENTS

| | | |
|---|---|---|
| 8,273,327 B2 | 9/2012 | Pathak et al. |
| 8,685,367 B2 | 4/2014 | Brandom et al. |
| 2009/0297612 A1 | 12/2009 | Koole et al. |
| 2010/0262182 A1 * | 10/2010 | Moszner ............ A61B 17/0057 606/213 |
| 2013/0225778 A1 | 8/2013 | Goodrich et al. |
| 2015/0110722 A1 | 4/2015 | Hohn et al. |
| 2016/0030602 A1 | 2/2016 | Dreher et al. |

FOREIGN PATENT DOCUMENTS

| | | | |
|---|---|---|---|
| DE | 102009036817 A1 * | 2/2011 | ......... A61B 17/0057 |
| EP | 0436316 | 7/1991 | |
| WO | 199221327 | 12/1992 | |
| WO | 2015033093 | 3/2015 | |

OTHER PUBLICATIONS

English Machine Translation of DE102009036817 A1, Printed Online Feb. 7, 2018.*
International Search Report and Written Opinion dated Apr. 21, 2016 for PCT/US2016/012820.
Galperin, et al., "Synthesis and Characterization of New Micrometer-Sized Radiopaque polymeric particles of Narrow Size Distribution by a Single-Step Swelling of Uniform Polystyrene Template Microspheres for X-Ray Imaging Applications", Biomacromolecules, vol. 7, No. 9,, 2006, 2650-2651.
Mawad et al., 'Synthesis and Characterization of Radiopaque Iodine-Containing Degradable PVA Hydrogels', Biomacromolecules, vol. 9 No. 1, 2008.
Radiopaque Bioactive Microspheres as Injectable Biomaterials, Printed by Datawyse, Universitaire Pers Maastricht, Copyright K. Saralidze, Maastricht 2008.
European Search Report dated Jul. 18, 2018 for EP16737667.2.
Brown, et al., Syntheses and Copolymerizations of New Water-Soluble Polyiodinated Acrylic Monomers, Makromoi Chem., Rapid Commun. 6 ,1985 ,503-507.

* cited by examiner

*Primary Examiner* — James W Rogers
(74) *Attorney, Agent, or Firm* — Stoel Rives LLP

(57) ABSTRACT

Radiopaque monomers, polymers, and microspheres are disclosed herein. Methods of using the radiopaque monomers, polymers, and microspheres are disclosed herein. Methods of manufacturing radiopaque monomers, polymers, and microspheres are disclosed herein.

20 Claims, 17 Drawing Sheets

RADIOPAQUE MONOMERS, POLYMERS, MICROSPHERES, AND METHODS RELATED THERETO

RELATED APPLICATIONS

This application claims priority to U.S. Provisional Application No. 62/102,384, filed on Jan. 12, 2015, titled RADIOPAQUE MONOMERS, POLYMERS, MICROSPHERES, AND METHODS RELATED THERETO, which is hereby incorporated by reference in its entirety.

TECHNICAL FIELD

The present disclosure relates generally to medical devices and methods of treatment. More specifically, the present disclosure relates to radiopaque monomers, polymers, microspheres, and methods related thereto.

BRIEF DESCRIPTION OF THE DRAWINGS

The embodiments disclosed herein will become more fully apparent from the following description and appended claims, taken in conjunction with the accompanying drawings. The drawings depict primarily generalized embodiments, which embodiments will be described with additional specificity and detail in connection with the drawings in which:

DETAILED DESCRIPTION

Figure 1:
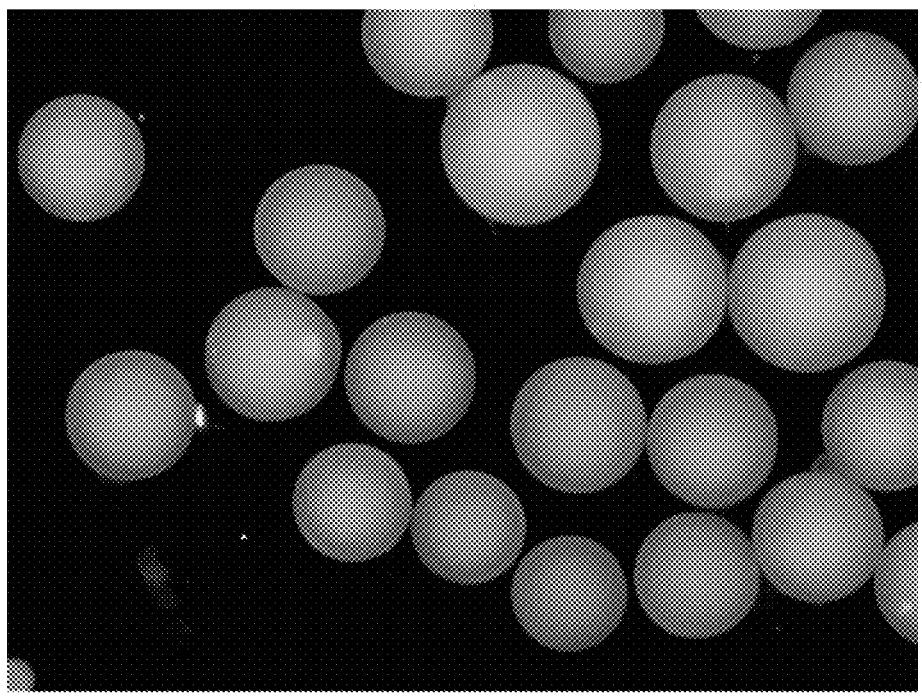
FIG. 1 is a micrograph of 300-500 micron diameter microspheres produced in Example 1, according to one embodiment.

Radiopaque monomers, polymers, microspheres, and methods related thereto are disclosed herein. It will be readily understood that the embodiments as generally described below and as illustrated in the examples and Figures could be modified in a wide variety of ways. Thus, the following more detailed description of various embodiments, as described below and represented in the examples and Figures, is not intended to limit the scope of the disclosure, but is merely representative of various embodiments.

The phrases "operably connected to," "connected to," and "coupled to" refer to any form of interaction between two or more entities, including mechanical, electrical, magnetic, electromagnetic, fluid, and thermal interaction. Two entities may interact with each other even though they are not in direct contact with each other. For example, two entities may interact with each other through an intermediate entity.

As used herein, the term "alkyl" as employed herein by itself or as part of another group refers to a saturated aliphatic hydrocarbon straight chain or branched chain group having, unless otherwise specified, 1 to 20 carbon atoms (whenever it appears herein, a numerical range such as "1 to 20" refers to each integer in the given range; e.g., "1 to 20 carbon atoms" means that the alkyl group can consist of 1, 2 or 3 carbon atoms, or more carbon atoms, up to a total of 20). An alkyl group can be in an unsubstituted form or substituted form with one or more substituents (generally one to three substituents can be present except in the case of halogen substituents, e.g., perchloro). For example, a $C_{1-6}$ alkyl group refers to a straight or branched aliphatic group containing 1 to 6 carbon atoms (e.g., including methyl, ethyl, propyl, isopropyl, butyl, sec-butyl, tert-butyl, 3-pentyl, hexyl, etc.), which can be optionally substituted.

As used herein, "lower alkyl" refers to an alkyl group having from 1 to 6 carbon atoms.

The term "cycloalkyl" as used herein by itself or as part of another group refers to a fully saturated 3- to 8-membered cyclic hydrocarbon ring (i.e., a cyclic form of an alkyl) alone ("monocyclic cycloalkyl") or fused to another cycloalkyl, cycloalkynyl, cycloalkenyl, heterocycle, aryl or heteroaryl ring (i.e., sharing an adjacent pair of carbon atoms with other such rings) ("polycyclic cycloalkyl"). Thus, a cycloalkyl can exist as a monocyclic ring, bicyclic ring, or a spiral ring. When a cycloalkyl is referred to as a $C_x$ cycloalkyl, this means a cycloalkyl in which the fully saturated cyclic hydrocarbon ring (which may or may not be fused to another ring) has x number of carbon atoms. When a cycloalkyl is recited as a substituent on a chemical entity, it is intended that the cycloalkyl moiety is attached to the entity through a single carbon atom within the fully saturated cyclic hydrocarbon ring of the cycloalkyl. In contrast, a substituent on a cycloalkyl can be attached to any carbon atom of the cycloalkyl. A cycloalkyl group can be unsubstituted or substituted with one or more substituents so long as the resulting compound is sufficiently stable and suitable for use. Examples of cycloalkyl groups include, for example, cyclopropyl, cyclobutyl, cyclopentyl, cyclohexyl and cycloheptyl.

The term "heterocycle" (or "heterocyclyl" or "heterocyclic" or "heterocyclo") as used herein by itself or as part of another group means a saturated or partially saturated 3-7 membered non-aromatic cyclic ring formed with carbon atoms and from one to four heteroatoms independently selected from the group consisting of O, N, and S, wherein the nitrogen and sulfur heteroatoms can be optionally oxidized, and the nitrogen can be optionally quaternized ("monocyclic heterocycle"). The term "heterocycle" also encompasses a group having the non-aromatic heteroatom-containing cyclic ring above fused to another monocyclic cycloalkyl, cycloalkynyl, cycloalkenyl, heterocycle, aryl or heteroaryl ring (i.e., sharing an adjacent pair of atoms with such other rings) ("polycyclic heterocycle"). Thus, a heterocycle can exist as a monocyclic ring, bicyclic ring, polycyclic or a spiral ring. When a heterocycle is recited as a substituent on a chemical entity, it is intended that the heterocycle moiety is attached to the entity through an atom within the saturated or partially saturated ring of the heterocycle. In contrast, a substituent on a heterocycle can be attached to any suitable atom of the heterocycle. In a "saturated heterocycle" the non-aromatic heteroatom-containing cyclic ring described above is fully saturated, whereas a "partially saturated heterocycle" contains one or more double or triple bonds within the non-aromatic heteroatom-containing cyclic ring regardless of the other ring it is fused to. A heterocycle can be in an unsubstituted form or substituted form with one or more substituents so long as the resulting compound is sufficiently stable and suitable for use.

Some examples of saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

As used herein, "aryl" by itself or as part of another group means an all-carbon aromatic ring with up to 7 carbon atoms in the ring ("monocylic aryl"). In addition to monocyclic aromatic rings, the term "aryl" also encompasses a group having the all-carbon aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic aryl"). When an aryl is referred to as a $C_x$ aryl, this means an aryl in which the all-carbon aromatic ring (which may or may not be fused to another ring) has x number of carbon atoms. When an aryl is recited as a substituent on a chemical entity, it is intended that the aryl moiety is attached to the entity through an atom within the all-carbon aromatic ring of the aryl. In contrast, a substituent on an aryl can be attached to any suitable atom of the aryl. Examples, without limitation, of aryl groups are phenyl, naphthalenyl and anthracenyl. An aryl can be in an unsubstituted form or substituted form with one or more substituents so long as the resulting compound is sufficiently stable and suitable for use.

The term "heteroaryl" as employed herein refers to a stable aromatic ring having up to 7 ring atoms with 1, 2, 3 or 4 hetero ring atoms in the ring which are oxygen, nitrogen or sulfur or a combination thereof ("monocylic heteroaryl"). In addition to monocyclic hetero-aromatic rings, the term "heteroaryl" also encompasses a group having the monocyclic hetero-aromatic ring above fused to another cycloalkyl, cycloalkynyl, cycloalkenyl, heterocycle, aryl or heteroaryl ring (i.e., sharing an adjacent pair of atoms with such other rings) ("polycyclic heteroaryl"). When a heteroaryl is recited as a substituent on a chemical entity, it is intended that the heteroaryl moiety is attached to the entity through an atom within the heteroaromatic ring of the heteroaryl. In contrast, a substituent on a heteroaryl can be attached to any suitable atom of the heteroaryl. A heteroaryl can be in an unsubstituted form or substituted form with one or more substituents so long as the resulting compound is sufficiently stable and suitable for use.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom can be in the form of an N-oxide, e.g., a pyridyl N-oxide, pyrazinyl N-oxide and pyrimidinyl N-oxide.

As used herein, "amino" refers to an —$NR^xR^y$ group, with $R^x$ and $R^y$ as defined herein.

As used herein, the term "ester" is a —$C(=O)OR^x$ group, where $R^x$ is as defined herein, except that it is not hydro (e.g., it is methyl, ethyl, or lower alkyl).

As used herein, the term "hydro" refers to a bound hydrogen atom (—H group).

As used herein, the term "hydroxy" refers to an —OH group.

$R^x$ and $R^y$ are independently selected from the group consisting of hydro, alkyl, cycloalkyl, aryl, heteroaryl, and heterocycle, each being optionally substituted.

In some embodiments of a monomer, the monomer has a structure according to Formula I:

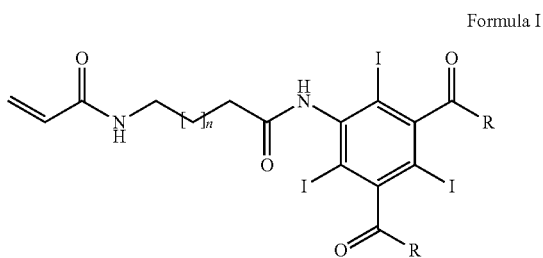

Formula I wherein n is 0-12 and wherein R is either an oxygen-containing moiety or a nitrogen-containing moiety.

In some embodiments of the monomer of Formula I, when R is an oxygen-containing moiety, an oxygen of the oxygen-containing moiety may be attached to the carbonyl adjacent to the R. By way of non-limiting example, R may be hydroxyl or a salt thereof or R may form an ester with the carbonyl adjacent to the R. Likewise, when R is a nitrogen-containing moiety, a nitrogen of the nitrogen-containing moiety may be attached to the carbonyl adjacent to the R. By way of non-limiting example, R may be an amino group, such as a secondary or tertiary amine. Non-limiting examples of substituents on the amino group include hydroxyalkyl and/or di-hydroxyalkyl.

In some embodiments of the monomer of Formula I, n is 0-8. Alternatively, n may be 0-6, 1-4, 1-3, 2, or 1.

In some embodiments of the monomer of Formula I, the monomer has a structure according to Formula Ia, Formula Ib, or a salt thereof.

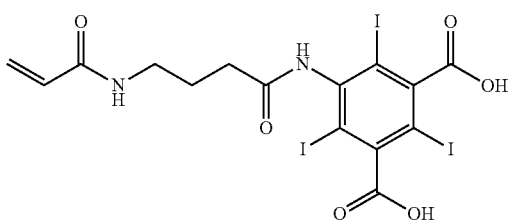

Formula Ia

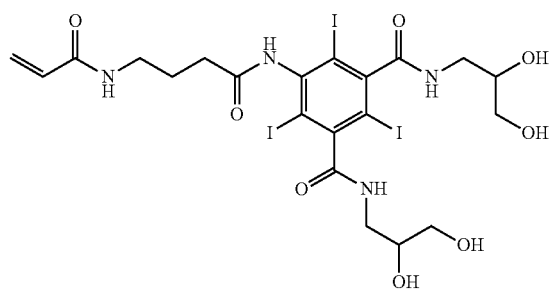

Formula Ib

In some embodiments of a polymer, the polymer comprises polymerized monomers of Formula I, wherein n is 0-12 and wherein R is either an oxygen-containing moiety or a nitrogen-containing moiety. It should be understood that the ethenyl group of a monomer of Formula I during polymerization forms part of the backbone of the polymer chain and is converted from a carbon-carbon double bond to a carbon-carbon single bond. The polymer may comprise at least about 20%, at least about 25%, at least about 30%, at least about 35%, at least about 40%, at least about 45%, at least about 50%, at least about 55%, at least about 60%, at least about 65%, at least about 70%, or at least about 75% of polymerized monomers of Formula I. All of the embodiments of the monomer of Formula I also apply to embodiments of the polymerized monomers of Formula I.

The polymer may further comprise polymerized acrylamide. Non-limiting examples of acrylamides include N-[Tris(hydroxymethyl)methyl]acrylamide (CAS No. 13880-05-2), N,N'-Methylenebis(acrylamide) (CAS No. 110-26-9), diethyl aminoethyl acrylamide, and triethyl aminoethyl acrylamide.

The polymer may further comprise a polymerized acrylic, acrylate, and/or methacrylate monomer, such as by way of non-limiting example, acrylic acid, methacrylate, and hydroxyethylmethacrylate.

The polymer may further comprise a cross-linker, such as by way of non-limiting example, glutaraldehyde. The polymer may further comprise a gelatin. The polymer may further comprise a coloring agent, such as by way of non-limiting example, polymerized N-acryloyl hexamethylene Procion Red HE-3B and/or a fluorone (e.g., rhodamine).

The polymer may further comprise an additional radiopaque agent, such as by way of non-limiting example, polymerized (acrylamido-3-propionamido)-3-triiodo-2,4,6-benzoic acid and/or barium sulfate.

The polymer may further comprise a magnetic agent (or magnetic contrast agent), such as a superparamagnetic iron oxide particle or contrast agent. Non-limiting examples of superparamagnetic iron oxide contrast agents include Ferucarbotran. Magnetic agents can be used with magnetic resonance imaging (MRI). In some embodiments, the magnetic agent (e.g., superparamagnetic iron oxide contrast agent) can be incorporated into the polymer. For example, in certain embodiments, the magnetic agent can be added to the monomers prior to polymerization. In such embodiments, the magnetic agent can be incorporated (e.g., gelled) into and/or throughout the polymer network.

In some embodiments of a microsphere, the microsphere comprises polymers comprising polymerized monomers of Formula I, wherein n is 0-12 and wherein R is either an oxygen-containing moiety or a nitrogen-containing moiety. All of the embodiments of polymers comprising polymerized monomers of Formula I also apply to such microsphere embodiments.

The microspheres may have a variety of diameters, such as, by way of non-limiting example, about 10 micron to about 2000 micron, about 30 micron to about 1500 micron, about 40 micron to about 1200 micron, about 40 micron to about 900 micron, about 40 micron to about 600 micron, and about 40 micron to about 400 micron.

The microsphere may be non-resorbable or resorbable within a body of a patient, depending upon how synthesized. For example, a resorbable microsphere may be synthesized by using a resorbable cross-linking monomer, as opposed to a non-resorbable cross-linking monomer, with one or more monomer embodiments disclosed herein.

The microsphere may comprise a coloring agent selected according to a size of the microsphere.

The microsphere may be shrinkable or swellable. As used herein, "swellable" microspheres refers to microspheres that are capable of being enlarged in size, yet retain substantially the same shape, upon certain conditions, such as contacting aqueous liquids or physiological fluids. In certain embodiments, the swellable microspheres can be enlarged up to about 15 times of their original diameter or to about 3,375 times their original volume. In certain embodiments, swellable microspheres are enlarged to at least four times their original diameter or 64 times in volume upon contact with saline (0.9% sodium chloride solution). In certain embodiments, swellable microspheres are enlarged to at least about 110%, at least about 115%, at least about 120%, at least about 125%, at least about 130%, at least about 135%, at least about 140%, at least about 145%, and/or at least about 150% their original diameter upon contact with water. In some embodiments "swellable" microspheres refers to microspheres that have the ability to absorb water. For example, in certain embodiments, the water absorption rate of a swellable microsphere is at least about 750 g/g. The degree of swelling can be controlled by controlling factors such as, for example, the solvents in which they are suspended, and specific polymers used to make the microspheres. In certain embodiments, the degree of cross-linking is adjusted, and in other embodiments, cross-linking is not adjusted or is not present. This property enables the microspheres to be injected through needles of, for example, 18 to 30 gauge or smaller, yet be enlarged and secured at the injection site and of sufficient size to avoid or reduce the chance of being eliminated by the lymphatic or immune system of the mammal.

As used herein, "shrinkable" microspheres refers to microspheres that are capable of being shrunk in size, yet retain substantially the same shape, upon certain conditions, such as contacting aqueous liquids or physiological fluids. In certain embodiments, the shrinkable microspheres can be shrunk to about 95%, about 90%, about 85%, about 80%, about 75%, about 70%, about 65%, about 60%, about 55%, and/or about 50% their original diameter upon contact with saline.

The microsphere may comprise a therapeutic agent. For example, the microsphere may be loaded with the therapeutic agent. The therapeutic agent may be adsorbed, absorbed, or otherwise associated with the microsphere. The microsphere may be configured to ionically interact with the therapeutic agent. For example, in embodiments in which acrylamides are used, the amino functionalities can be protonated to create positively charged groups. Likewise, in embodiments in which acrylic acids are used, negatively charged groups can be created by deprotonating the acid functionality. In another example, in embodiments in which acrylic esters are used, ionic groups can be generated by hydrolyzing the ester groups. Ionic groups can also be generated by using suitable cross-linkers, in which case the resulting polymer or copolymer is cross-linked.

The therapeutic agent may comprise a drug, such as, by way of non-limiting example, an anti-neoplastic drug. Examples of drugs include, but are not limited to, doxorubicin, irinotecan, paclitaxel, vinblastine, cisplatin, and methotrexate.

In some embodiments of methods of embolization, the methods comprise injecting into a blood vessel of a patient a microsphere comprising polymers comprised of polymerized monomers of Formula I, wherein n is 0-12 and wherein R is either an oxygen-containing moiety or a nitrogen-containing moiety. The embolization may be for treating a tumor, treating a varicocele, ablating an organ, preventing hemorrhage, or occluding a vascular anomaly.

In some embodiments of methods of tracking a microsphere, the methods comprise introducing a microsphere comprising polymers comprised of polymerized monomers of Formula I, wherein n is 0-12 and wherein R is either an oxygen-containing moiety or a nitrogen-containing moiety, into a blood vessel or tissue of a patient, imaging at least a portion of the patient, and determining a location of the microsphere. A contrast agent may not be substantially present (e.g., mostly dissipated or never injected) in the location of the microsphere at the time of imaging.

In some embodiments of methods of treating a disease, a disorder, or a cosmetic need of a patient, the methods comprise injecting a microsphere comprising polymers comprised of polymerized monomers of Formula I, wherein n is 0-12 and wherein R is either an oxygen-containing moiety or a nitrogen-containing moiety, into a blood vessel or tissue of the patient. The disease or disorder may comprise urinary incontinence, vesicoureteral reflux, vocal cord augmentation, cancer, or uterine fibroids. The cosmetic need may comprise wrinkles in the skin, lipoatrophy, acne scars, or a loss of fat in the lips or other area of the body.

All of the embodiments of microspheres disclosed above may be used in the methods of embolization, methods of tracking a microsphere, and methods of treating a disease, a disorder, or a cosmetic need of a patient.

The methods may each further comprise detecting a location of the microsphere without use of a separate contrast agent.

The methods may each further comprise loading the microsphere with a therapeutic agent prior to injecting the microsphere.

The methods may each further comprise detecting a location of the microsphere more than about 24 hours after injection of the microsphere.

The methods may each further comprise detecting a location of the microsphere more than about 48 hours after injection of the microsphere.

The methods may each further comprise detecting a location of the microsphere more than about a week after injection of the microsphere.

The methods may each further comprise detecting a location of the microsphere more than about a month after injection of the microsphere.

The blood vessel for each of the methods described herein may comprise a hepatic artery, prostatic artery, or uterine artery.

The methods may each further comprise injecting a contrast agent prior to injecting the microsphere to determine an arterial structure of the patient and then after injecting the microsphere, detecting a location of the microsphere after the contrast agent has dissipated.

The methods may each be used when the patient is allergic to conventional contrast agents.

In some embodiments of methods of making a monomer of Formula I, the methods comprise:

reacting a compound having a structure according to Formula A with a compound having a structure according to Formula B,

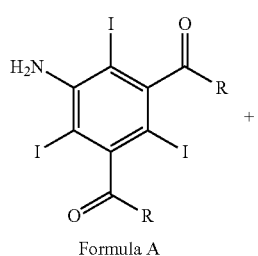

Formula A

-continued

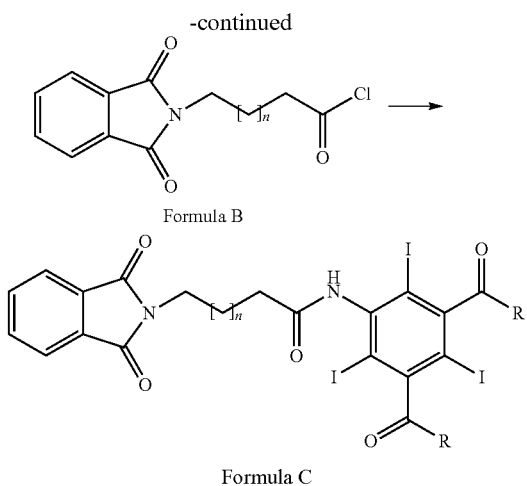

Formula B

Formula C to form a compound having a structure according to Formula C,

Formula C

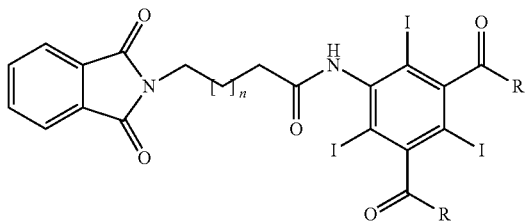

wherein R and n are as defined for Formula I, deprotecting the nitrogen of the phthalamide group of the compound having a structure according to Formula C to form a primary amine;

reacting the primary amine with a compound having a structure according to Formula D, Formula D to form a monomer having a structure according to Formula I. With the benefit of the present disclosure, one of ordinary skill would also be able to make a monomer having a structure according to Formula I via other methods.

In some embodiments of methods of making a polymer, the methods comprise polymerizing a monomer having a structure according to Formula I.

In some embodiments of methods of making a microsphere, the methods comprise polymerizing a monomer having a structure according to Formula I in a manner sufficient to form polymer microspheres, such as in an oil suspension.

EXAMPLES

The following examples all used a paraffin oil suspension for the synthesis of the microspheres. Disodium 5-(4-acrylamidobutanamido)-2,4,6-triiodoisophthalate ("Monomer Ia") was used in the examples (i.e., the sodium salt of the monomer having a structure according to Formula Ia). The Monomer Ia was 85-87% pure. All monomers were solubilized in water or acetate (pH 6). The disodium 5-(4-acrylamidobutanamido)-2,4,6-triiodoisophthalate solution was prepared at room temperature. MBA (N,N'-Methylenebis(acrylamide), CAS 110-26-9) was used as a water-soluble cross-linker at 10 or 20% (molar ratio). Ammonium persulfate was used as a water-soluble initiator. TEMED (N,N,N',N'-Tetramethylethylenediamine) was used as an activator in the continuous phase. Arlacel 83/Span 83 (Sorbitan sesquioleate, CAS 8007-43-0) was used as a surfactant in the continuous phase.

After all the washes (water and saline), the microspheres in saline were sieved on stainless steel sieves with the following mesh sizes: 500, 400, 300, 250, 106, and 25 microns. Microspheres with diameters from 100 to 300 microns were obtained on the 106 micron sieve and microspheres with diameters from 300 to 500 microns were obtained on the 300 micron sieve.

Example 1

7 Mole % Monomer Ia/10 Mole % MBA/250 mL Monomer Phase 8.08 g of Monomer Ia were dissolved in 75 mL of acetate buffer solution at 25-30° C. (1.4 M NaCl, 0.3 M sodium acetate trihydrate, water/glycerin 3/4 v/v, pH adjusted at 6 with acetic acid). The total volume was adjusted at 100 mL with water and filtered.

22.58 g of Trisacryl (N-[Tris(hydroxymethyl)methyl] acrylamide, CAS 13880-05-2) and 2.61 g of MBA were dissolved in 100 mL of the same acetate buffer solution at 40° C., and the volume was adjusted at 150 mL with water and filtered.

The two solutions were mixed and stirred at room temperature for a few minutes.

The initiator was added (0.43 g of ammonium persulfate) and the monomer solution was poured quickly into 1 L of paraffin oil containing 0.75 g of Arlacel 83 and 1 mL of TEMED at 60° C. under mechanical stirring at 200 rpm.

After 50 minutes the polymerization reaction was stopped and the microspheres were washed extensively with water and saline solution (0.9% NaCl). FIG. 1 illustrates the microspheres produced in Example 1 with diameters of about 300-500 microns.

Example 2

14 Mole % Monomer Ia/10 Mole % MBA/250 mL Monomer Phase 13.82 g of Monomer Ia were dissolved in 75 mL of acetate buffer solution at 25-30° C. (1.4 M NaCl, 0.3 M sodium acetate trihydrate, water/glycerin 3/4 v/v, pH adjusted at 6 with acetic acid). The total volume was adjusted at 100 mL with water and filtered.

17.86 g of Trisacryl (N-[Tris(hydroxymethyl)methyl] acrylamide, CAS 13880-05-2) and 2.05 g of MBA were dissolved in 95 mL of the same acetate buffer solution at 40° C., and the volume was adjusted at 150 mL with water and filtered.

The two solutions were mixed and stirred at room temperature for a few minutes.

The initiator was added (0.37 g of ammonium persulfate) and the monomer solution was poured quickly into 1 L of paraffin oil containing 0.86 g of Arlacel 83 and 1 mL of TEMED at 60° C. under mechanical stirring at 200 rpm.

Figure 2:
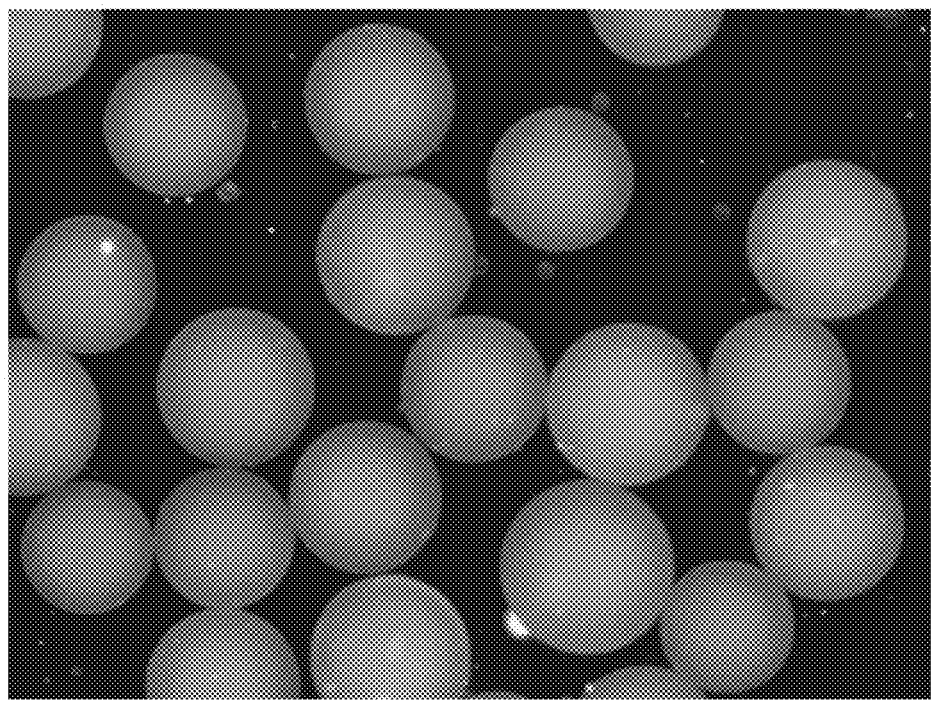
FIG. 2 is a micrograph of 300-500 micron diameter microspheres produced in Example 2, according to one embodiment.

After 55 minutes the polymerization reaction was stopped and the microspheres were washed extensively with water and saline solution (0.9% NaCl). FIG. 2 illustrates the microspheres produced in Example 2 with diameters of about 300-500 microns.

Example 3

21 Mole % Monomer Ia/10 Mole % MBA/250 mL Monomer Phase 17.95 g of Monomer Ia were dissolved in 75 mL of acetate buffer solution at 25° C. (1.4 M NaCl, 0.3 M sodium acetate trihydrate, water/glycerin 3/4 v/v, pH adjusted at 6 with acetic acid). The total volume was adjusted at 100 mL with water and filtered.

14.07 g of Trisacryl (N-[Tris(hydroxymethyl)methyl] acrylamide, CAS 13880-05-2) and 1.83 g of MBA were dissolved in 95 mL of the same acetate buffer solution at 40° C., and the volume was adjusted at 150 mL with water and filtered.

The two solutions were mixed and stirred at room temperature for a few minutes.

The initiator was added (0.37 g of ammonium persulfate) and the monomer solution was poured quickly into 1 L of paraffin oil containing 0.86 g of Arlacel 83 and 1 mL of TEMED at 60° C. under mechanical stirring at 200 rpm.

Figure 3:
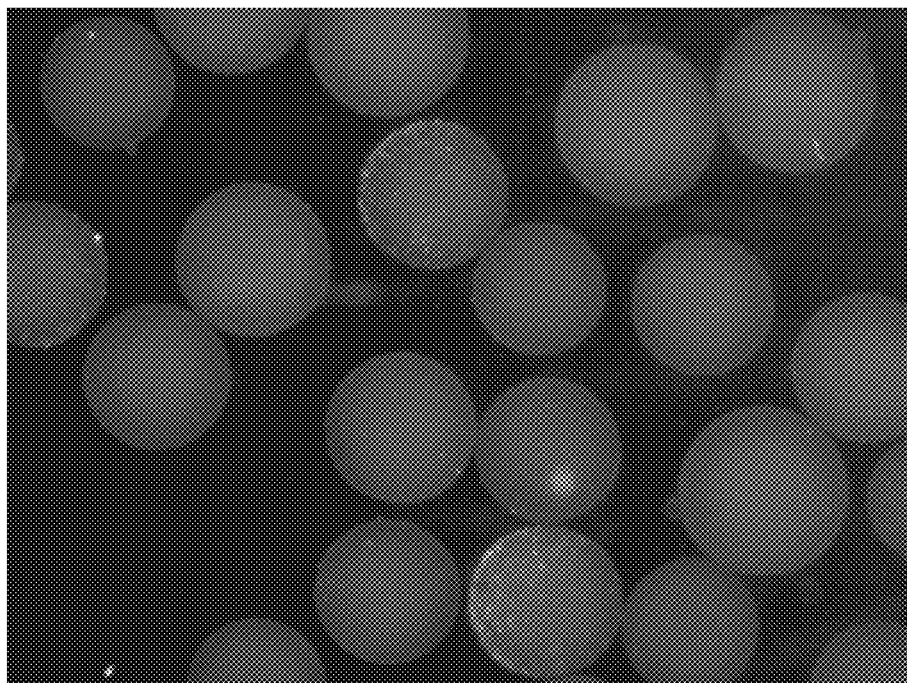
FIG. 3 is a micrograph of 300-500 micron diameter microspheres produced in Example 3, according to one embodiment.

After 50 minutes the polymerization reaction was stopped and the microspheres were washed extensively with water and saline solution (0.9% NaCl). FIG. 3 illustrates the microspheres produced in Example 3 with diameters of about 300-500 microns.

Example 4

41 Mole % Monomer Ia/10 Mole % MBA/275 mL Monomer Phase 25.55 g of Monomer Ia were dissolved in 125 mL of acetate buffer solution at 24° C. (1.4 M NaCl, 0.3 M sodium acetate trihydrate, water/glycerin 3/4 v/v, pH adjusted at 6 with acetic acid). The total volume was adjusted at 200 mL with water and filtered.

7.09 g of Trisacryl (N-[Tris(hydroxymethyl)methyl] acrylamide, CAS 13880-05-2) and 1.30 g of MBA were dissolved in 50 mL of the same acetate buffer solution at 40° C., and the volume was adjusted at 75 mL with water and filtered.

The two solutions were mixed and stirred at room temperature for a few minutes.

The initiator was added (0.34 g of ammonium persulfate) and the monomer solution was poured quickly into 1 L of paraffin oil containing 0.93 g of Arlacel 83 and 1 mL of TEMED at 60° C. under mechanical stirring at 200 rpm.

Figure 4:
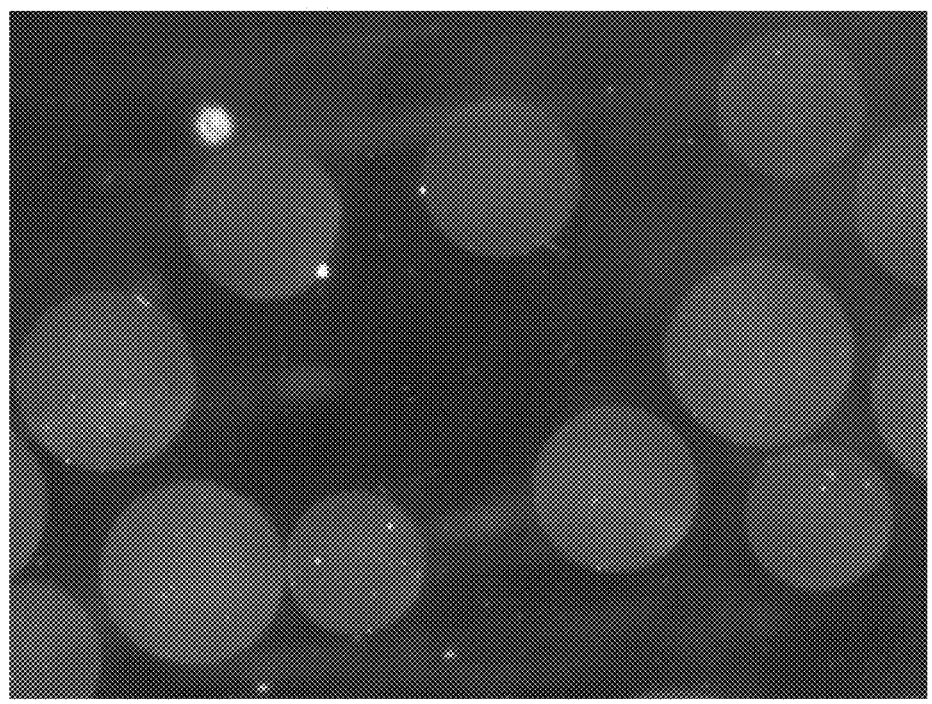
FIG. 4 is a micrograph of 300-500 micron diameter microspheres produced in Example 4, according to one embodiment.

After 51 minutes the polymerization reaction was stopped and the microspheres were washed extensively with water and saline solution (0.9% NaCl). FIG. 4 illustrates the microspheres produced in Example 4 with diameters of about 300-500 microns.

Example 5

21 Mole % Monomer Ia/20% Mole MBA/250 mL Monomers Phase 18.06 g of Monomer Ia were dissolved in 75 mL of acetate buffer solution at 25° C. (1.4 M NaCl, 0.3 M sodium acetate trihydrate, water/glycerin 3/4 v/v, pH adjusted at 6 with acetic acid). The total volume was adjusted at 100 mL with water and filtered.

12.12 g of Trisacryl (N-[Tris(hydroxymethyl)methyl] acrylamide, CAS 13880-05-2) and 3.61 g of MBA were dissolved in 95 mL of the same acetate buffer solution at 40-50° C., and the volume was adjusted at 150 mL with water and filtered.

The two solutions were mixed and stirred at room temperature for a few minutes.

The initiator was added (0.36 g of ammonium persulfate) and the monomer solution was poured quickly into 1 L of paraffin oil containing 1.01 g of Arlacel 83 and 1 mL of TEMED at 60° C. under mechanical stirring at 200 rpm.

Figure 5:
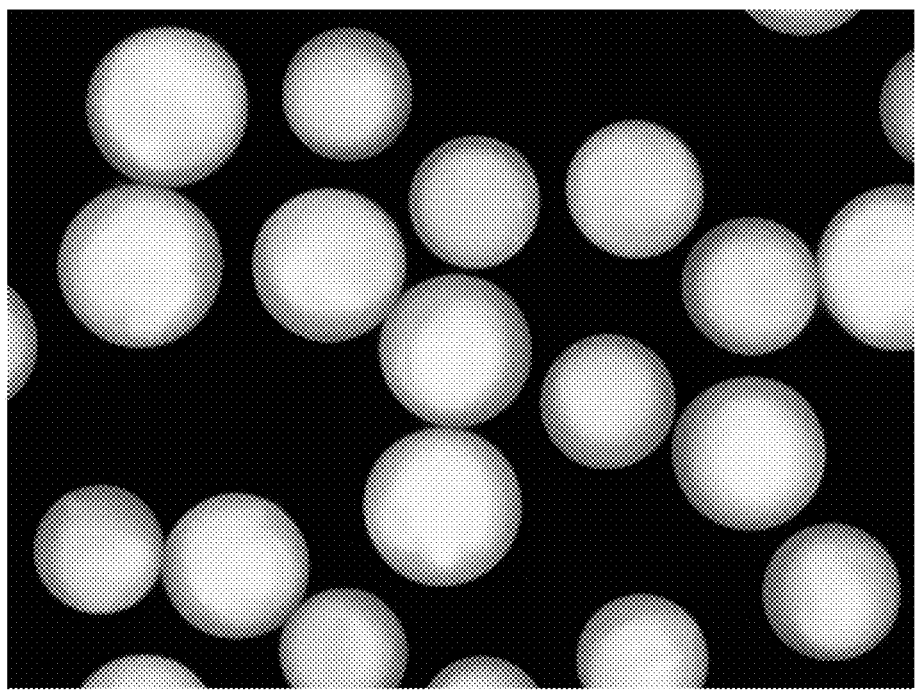
FIG. 5 is a micrograph of 300-500 micron diameter microspheres produced in Example 5, according to one embodiment.

After 45 minutes the polymerization reaction was stopped and the microspheres were washed extensively with water and saline solution (0.9% NaCl). FIG. 5 illustrates the microspheres produced in Example 5 with diameters of about 300-500 microns.

Example 6

41 Mole % Monomer Ia/20 Mole % MBA/255 mL Monomers Phase 25.62 g of Monomer Ia were dissolved in 125 mL of acetate buffer solution at 25° C. (1.4 M NaCl, 0.3 M sodium acetate trihydrate, water/glycerin 3/4 v/v, pH adjusted at 6 with acetic acid). The total volume was adjusted at 180 mL with water and filtered.

5.61 g of Trisacryl (N-[Tris(hydroxymethyl)methyl] acrylamide, CAS 13880-05-2) and 2.57 g of MBA were dissolved in 50 mL of the same acetate buffer solution at 40-60° C., and the volume was adjusted at 75 mL with water and filtered.

The two solutions were mixed and stirred at room temperature for a few minutes.

The initiator was added (0.36 g of ammonium persulfate) and the monomer solution was poured quickly into 1 L of paraffin oil containing 0.99 g of Arlacel 83 and 1 mL of TEMED at 60° C. under mechanical stirring at 200 rpm.

Figure 6:
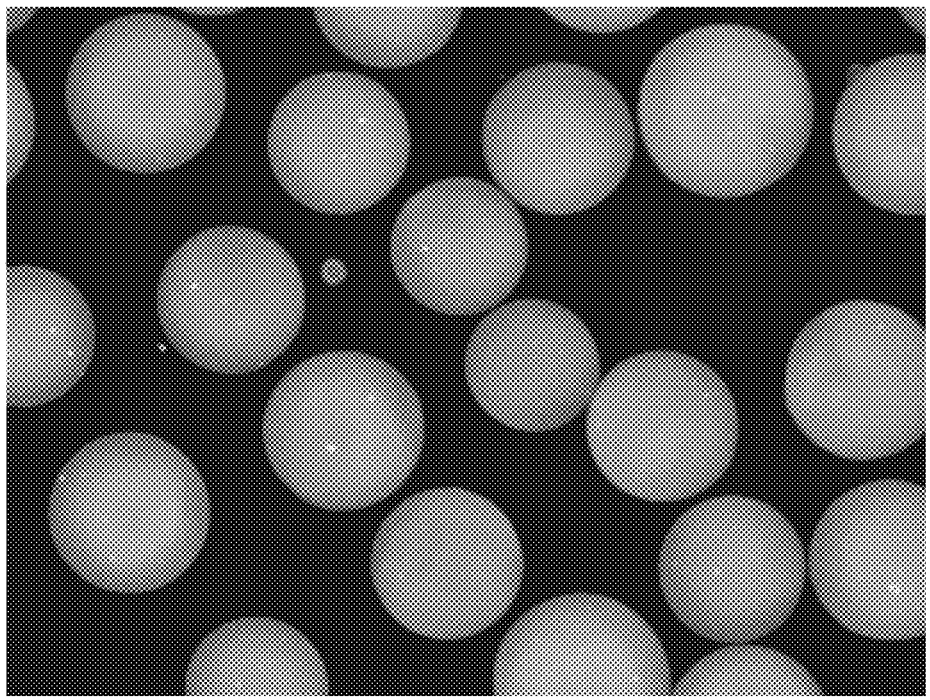
FIG. 6 is a micrograph of 300-500 micron diameter microspheres produced in Example 6, according to one embodiment.

After 45 minutes the polymerization reaction was stopped and the microspheres were washed extensively with water and saline solution (0.9% NaCl). FIG. 6 illustrates the microspheres produced in Example 6 with diameters of about 300-500 microns.

Example 7

42 Mole % Monomer Ia/20 Mole % MBA/140 mL Monomers Phase 25.97 g of Monomer Ia were dissolved in 100 mL of acetate buffer solution at 21° C. (1.4 M NaCl, 0.3 M sodium acetate trihydrate in water, pH adjusted at 6 with acetic acid). The total solution was filtered.

5.57 g of Trisacryl (N-[Tris(hydroxymethyl)methyl] acrylamide, CAS 13880-05-2) and 2.54 g of MBA were dissolved in 25 mL of the same acetate buffer solution at 60° C., and the volume was adjusted at 40 mL with water and filtered.

The two solutions were mixed and stirred at room temperature for a few minutes.

The initiator was added (0.34 g of ammonium persulfate) and the monomer solution was poured quickly into 1 L of paraffin oil containing 1.01 g of Arlacel 83 and 1 mL of TEMED at 60° C. under mechanic stirring at 180 rpm.

Figure 7:
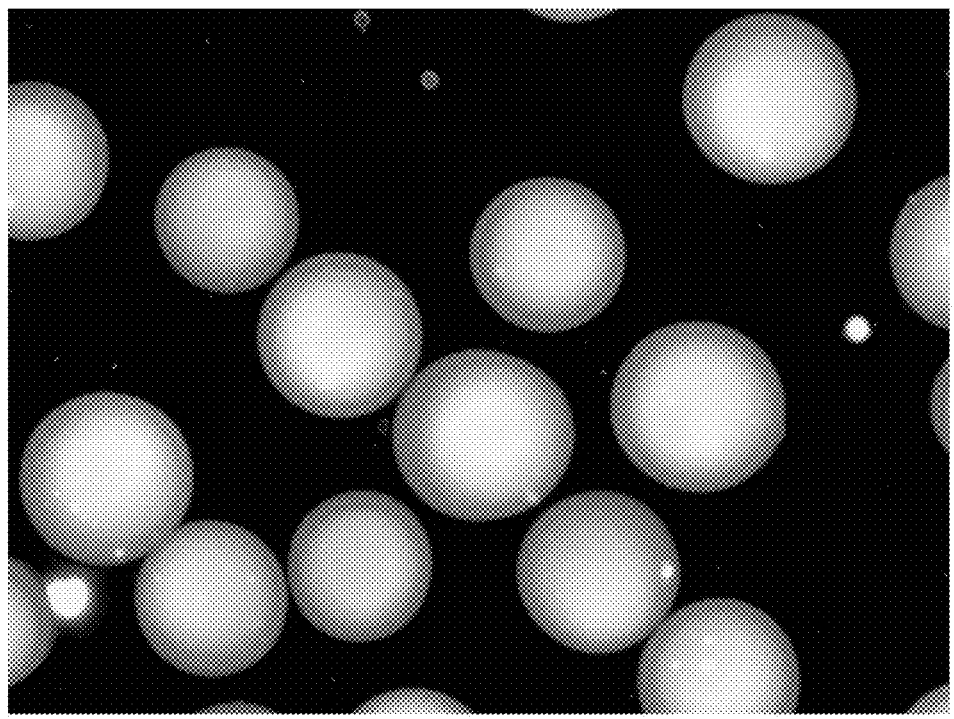
FIG. 7 is a micrograph of 300-500 micron diameter microspheres produced in Example 7, according to one embodiment.

After 50 minutes the polymerization reaction was stopped and the microspheres were washed extensively with water and saline solution (0.9% NaCl). FIG. 7 illustrates the microspheres produced in Example 7 with diameters of about 300-500 microns.

Example 8

79 Mole % Monomer Ia/21 Mole % MBA/120 mL Monomers Phase 31.36 g of Monomer Ia were dissolved in 75 mL of acetate buffer solution at 21° C. (1.4 M NaCl, 0.3 M sodium acetate trihydrate in water, pH adjusted at 6 with acetic acid). The total solution was filtered.

1.74 g of MBA was dissolved in 45 mL of the same acetate buffer solution at 30° C., and the solution was filtered.

The two solutions were mixed and stirred at room temperature for a few minutes.

The initiator was added (0.39 g of ammonium persulfate) and the monomer solution was poured quickly into 1 L of paraffin oil containing 1.00 g of Arlacel 83 and 1 mL of TEMED at 60° C. under mechanic stirring at 210 rpm.

Figure 8:
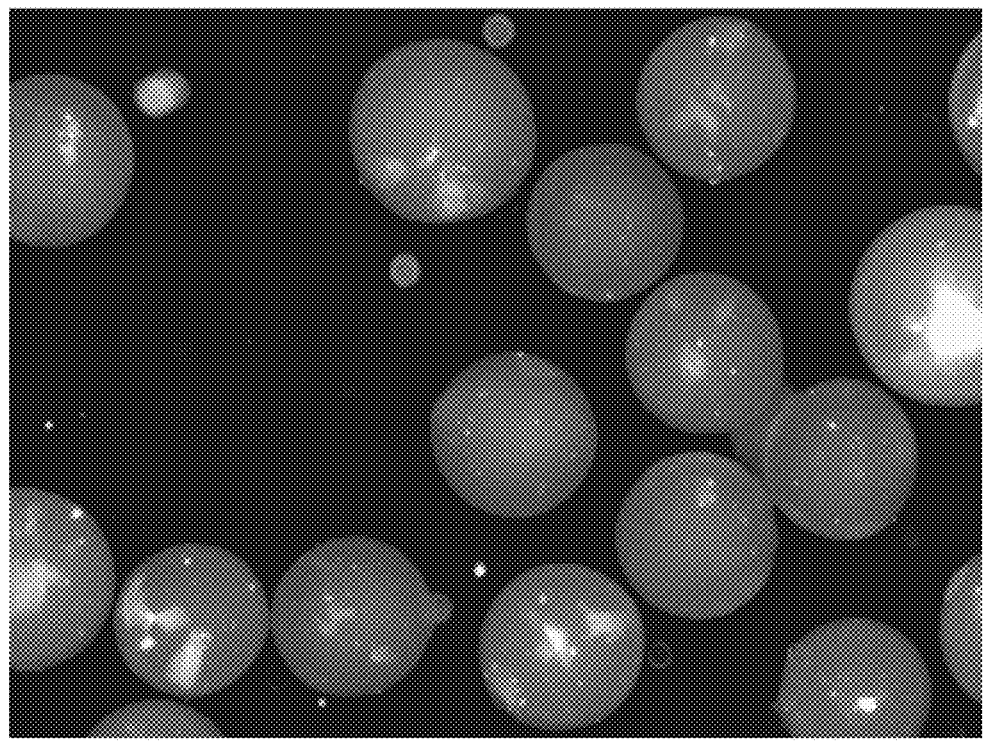
FIG. 8 is a micrograph of 300-500 micron diameter microspheres produced in Example 8, according to one embodiment.

After 60 minutes the polymerization reaction was stopped and the microspheres were washed extensively with water and saline solution (0.9% NaCl). FIG. 8 illustrates the microspheres produced in Example 8 with diameters of about 300-500 microns.

Example 9

Figure 9:
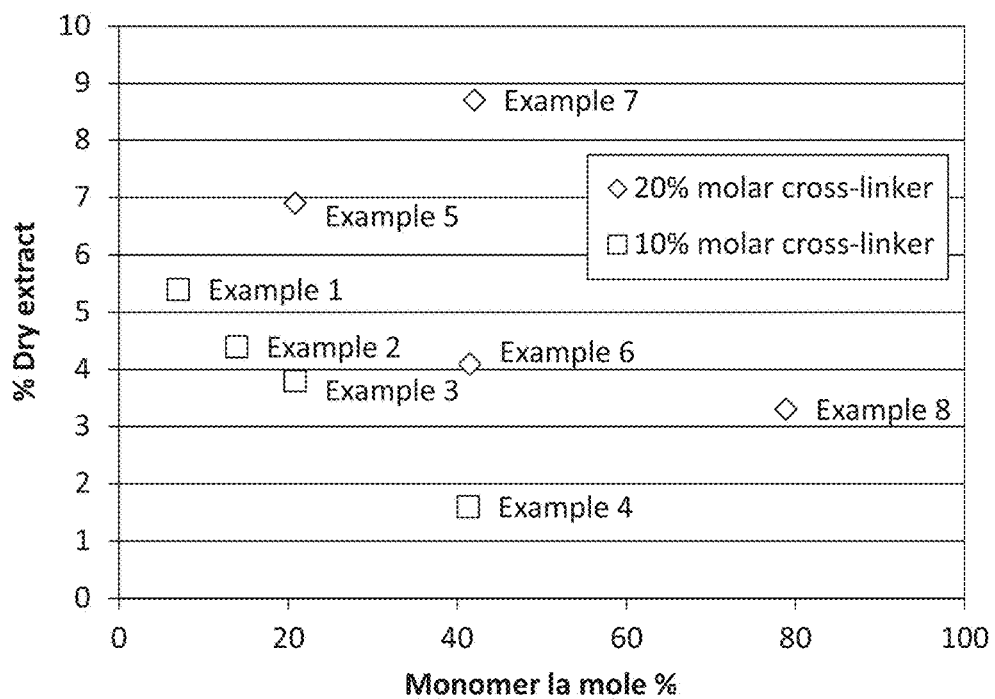
FIG. 9 is a graph that depicts the percent dry extract of the microspheres illustrated in FIGS. 1-8.

The percent dry content was calculated for the microspheres of Examples 1-8. The results are shown in Table 1. The dry extract represents the percentage left in mass when the microspheres are dried. The microspheres were washed with water, then frozen and dried in a freeze-dryer (lyophilization). FIG. 9 depicts the dry extract as a function of Monomer Ia mole percent and cross-linker (MBA) mole percent.

TABLE 1

| | Total volume of monomer solution | Monomer Ia (mol %) | MBA (mol %) | % dry content |
|---|---|---|---|---|
| Example 1 | 250 mL | 7.0% | 10.8% | 5.4% |
| Example 2 | 250 mL | 13.9% | 9.9% | 4.4% |
| Example 3 | 250 mL | 20.8% | 10.2% | 3.8% |
| Example 4 | 275 mL | 41.3% | 10.1% | 1.6% |
| Example 5 | 250 mL | 20.8% | 20.0% | 6.9% |
| Example 6 | 255 mL | 41.5% | 20.0% | 4.1% |
| Example 7 | 140 mL | 42.0% | 19.8% | 8.7% |
| Example 8 | 120 mL | 78.9% | 21.1% | 3.3% |

Example 10

The iodine content was determined by calculations (theoretical) and by chemical analysis (on dry 300-500 micron microspheres). The method to determine the percentage of iodine on a dry sample was: combustion of the sample in a Schoninger flask and dosage of iodide ions by ionic chromatography with U.V. detection.

TABLE 2

| | Total volume of monomer solution | Monomer Ia (mol %) | MBA (mol %) | % iodine (in mass) | |
|---|---|---|---|---|---|
| | | | | theoretical | analytical |
| Example 1 | 250 mL | 7.0% | 10.8% | 12.5% | 8.73% |
| Example 2 | 250 mL | 13.9% | 9.9% | 21.0% | 13.73% |
| Example 3 | 250 mL | 20.8% | 10.2% | 27.2% | 18.54% |
| Example 4 | 275 mL | 41.3% | 10.1% | 38.6% | 28.51% |
| Example 5 | 250 mL | 20.8% | 20.0% | 27.4% | 18.91% |
| Example 6 | 255 mL | 41.5% | 20.0% | 38.9% | 30.20% |
| Example 7 | 140 mL | 42.0% | 19.8% | 39.1% | 32.16% |
| Example 8 | 120 mL | 78.9% | 21.1% | 48.6% | 42.73% |

Conclusions: Iodine was present in the microspheres. There is less iodine in microspheres than the theoretical maximum. The ratio between the analytical and the theoretical percentage of iodine is about 65-70% for the three examples tested.

Example 11

The shrinkage or swelling behavior of some of the microspheres was studied.

Acidification of carboxylate groups of Monomer Ia was used to make the microspheres shrink in order to increase the dry content (and the concentration of iodine in dry microspheres).

Hydrochloric acid (2N) was added to a few milliliters of microspheres from Example 7 (300-500 μm) in saline (pH 5.65), to obtain a pH of 2.80. A granulometry analysis was done to check the size of the microspheres. Hydrochloric acid was added again to reach pH 1.4. A granulometry analysis was done to check the size of the microspheres. The results are shown in Table 3.

TABLE 3

| | Saline | Saline pH 2.8 | Saline pH 1.4 |
|---|---|---|---|
| Mean diameter (width - μm) | 402.07 | 379.75 | 260.34 |
| Ratio/Saline | (1.00) | 0.94 | 0.65 |

Figure 10:
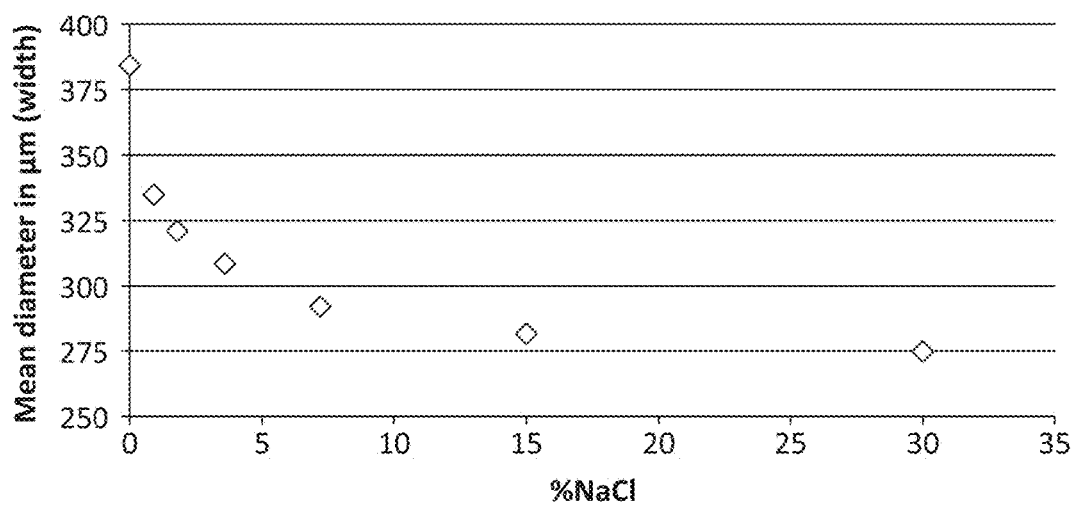
FIG. 10 is a graph that depicts mean diameters of Example 4 microspheres (200-400 μm) as a function of sodium chloride concentration.

The microspheres at pH 1.4 were then washed with water, frozen, and dried. The dry extract was 17.65% (compared to 8.7% before acidification). About 10 mL of microspheres from Example 4 (200-400 μm) in saline were washed in sodium chloride solutions at different concentrations and then measured by granulometry analysis. FIG. 10 depicts mean diameters of Example 4 microspheres (200-400 μm) as a function of sodium chloride concentration.

TABLE 4

| | | Example 4 (200-400 μm) | | | | | | |
|---|---|---|---|---|---|---|---|---|
| | | Water | Saline | Saline × 2 | Saline × 4 | Saline × 8 | buffer solution | Saline × 17 | Saline × 33 |
| % NaCl | | 0 | 0.9 | 1.8 | 3.6 | 7.2 | 8.3 | 15 | 30 |
| Number measured | | 312 | 312 | 318 | 327 | 331 | 325 | 352 | 342 |
| Mean diameter | Length | 395.31 | 343.73 | 327.85 | 313.89 | 297.30 | 292.49 | 288.49 | 281.70 |
| (μm) | Width | 384.34 | 334.92 | 321.06 | 308.57 | 292.05 | 285.54 | 281.63 | 274.84 |
| Swelling ratio/ | Length | 1.15 | 1.00 | 0.95 | 0.91 | 0.86 | 0.85 | 0.84 | 0.82 |
| Saline | Width | 1.15 | 1.00 | 0.96 | 0.92 | 0.87 | 0.85 | 0.84 | 0.82 |
| mean ratio (μm) | | 1.15 | 1.00 | 0.96 | 0.92 | 0.87 | 0.85 | 0.84 | 0.82 |

Example 12

Figure 11:
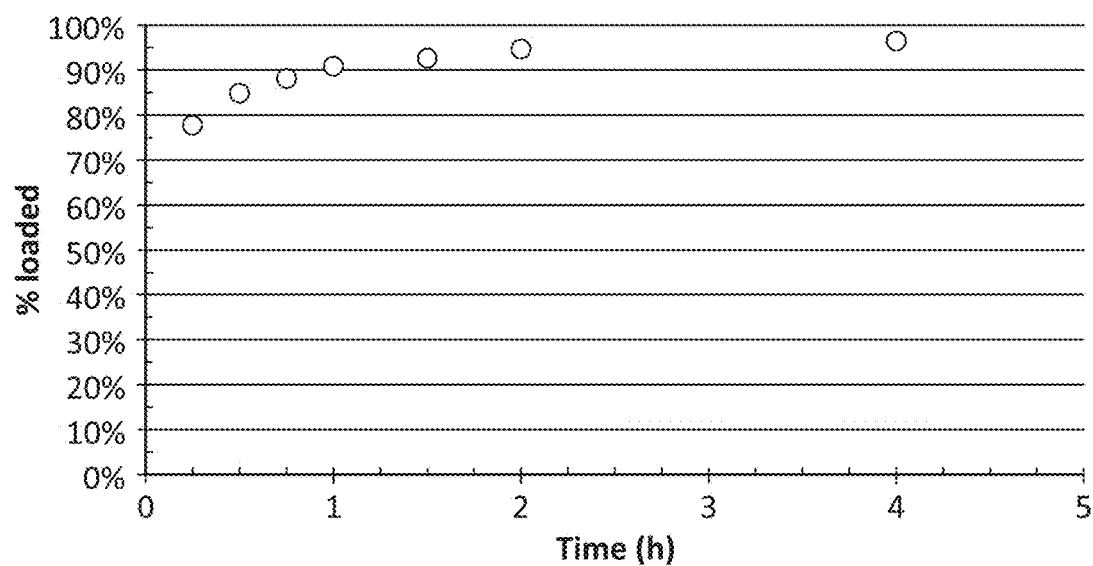
FIG. 11 is a graph that depicts Doxorubicin loading over time with microspheres from Example 7 (100-300 μm).
Figure 12:
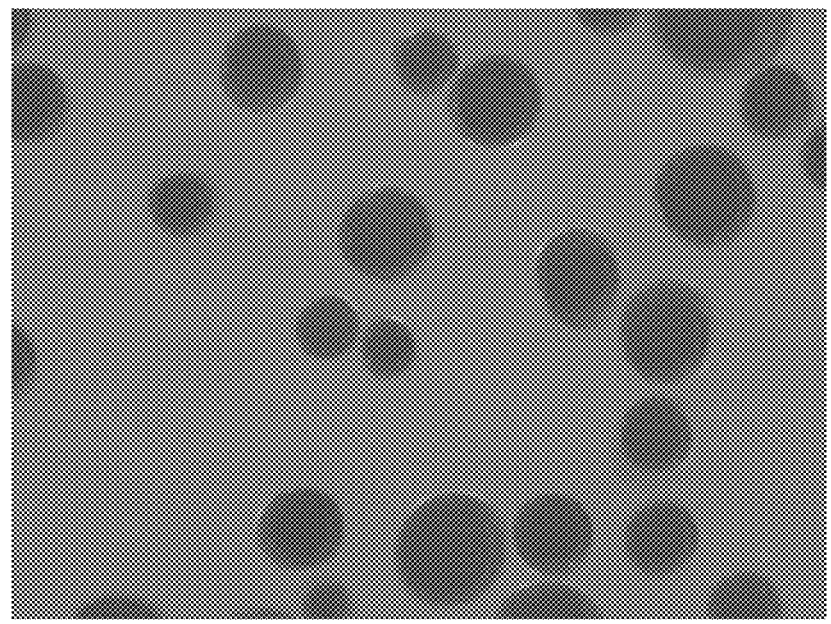
FIG. 12 is a micrograph of 100-300 micron diameter microspheres of Example 7 loaded with Doxorubicin.

The capability of example microspheres to load the anticancer drug Doxorubicin was tested with microspheres from Example 7. To 2 mL of microspheres from Example 7 (100-300 μm), a solution of Doxorubicin (Actavis, 50 mg/20 mL) was added. Aliquots of the supernatant were taken at different time points and then analyzed by HPLC to determine the concentration of Doxorubicin (and so to determine the percentage of loading). FIG. 11 illustrates Doxorubicin loading over time with microspheres from Example 7 (100-300 μm). FIG. 12 depicts the loaded microspheres. It was noted that after loading, the microspheres were slightly smaller (the swelling ratio was about 0.95, as compared to before the loading step).

Example 13

Figure 13:
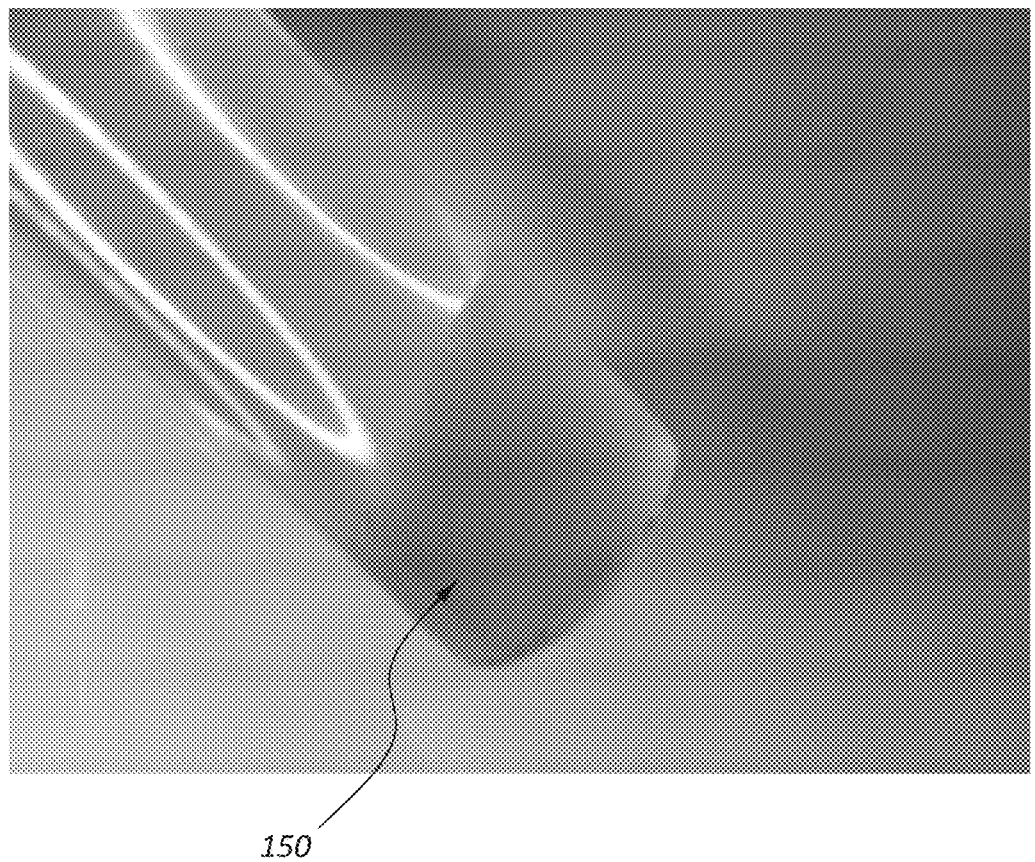
FIG. 13 depicts a picture of microspheres of Example 8 settled to the bottom of a vial filled with saline.
Figure 14:
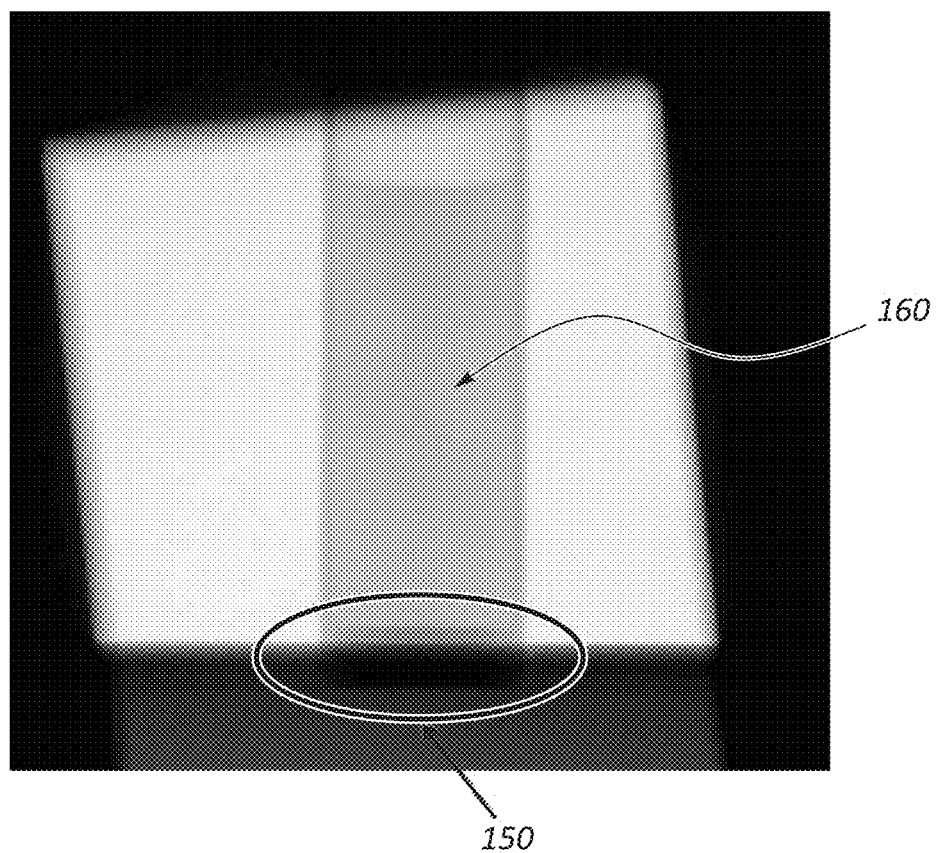
FIG. 14 depicts an X-ray image of the vial pictured in FIG. 13.

A vial was partially filled with saline and the microspheres of Example 8. FIG. 13 depicts a picture of microspheres 150 of Example 8 settled to the bottom of a vial filled with saline. FIG. 14 depicts an X-ray image of the vial pictured in FIG. 13, illustrating that under X-ray the settled microspheres 150 are darker than the saline 160.

Example 14

Figure 15:
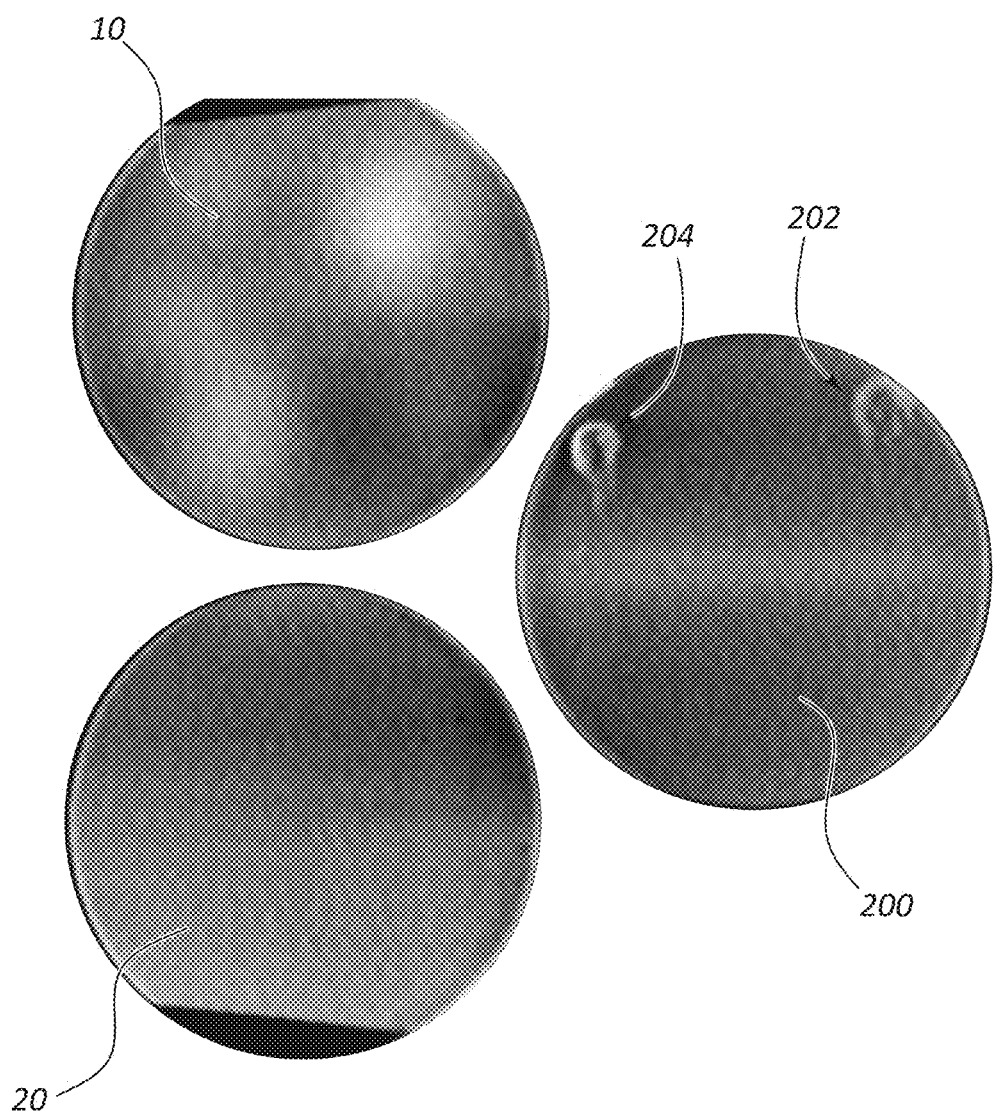
FIG. 15 depicts an X-ray image of a petri dish with microspheres of Example 7.
Figure 16:
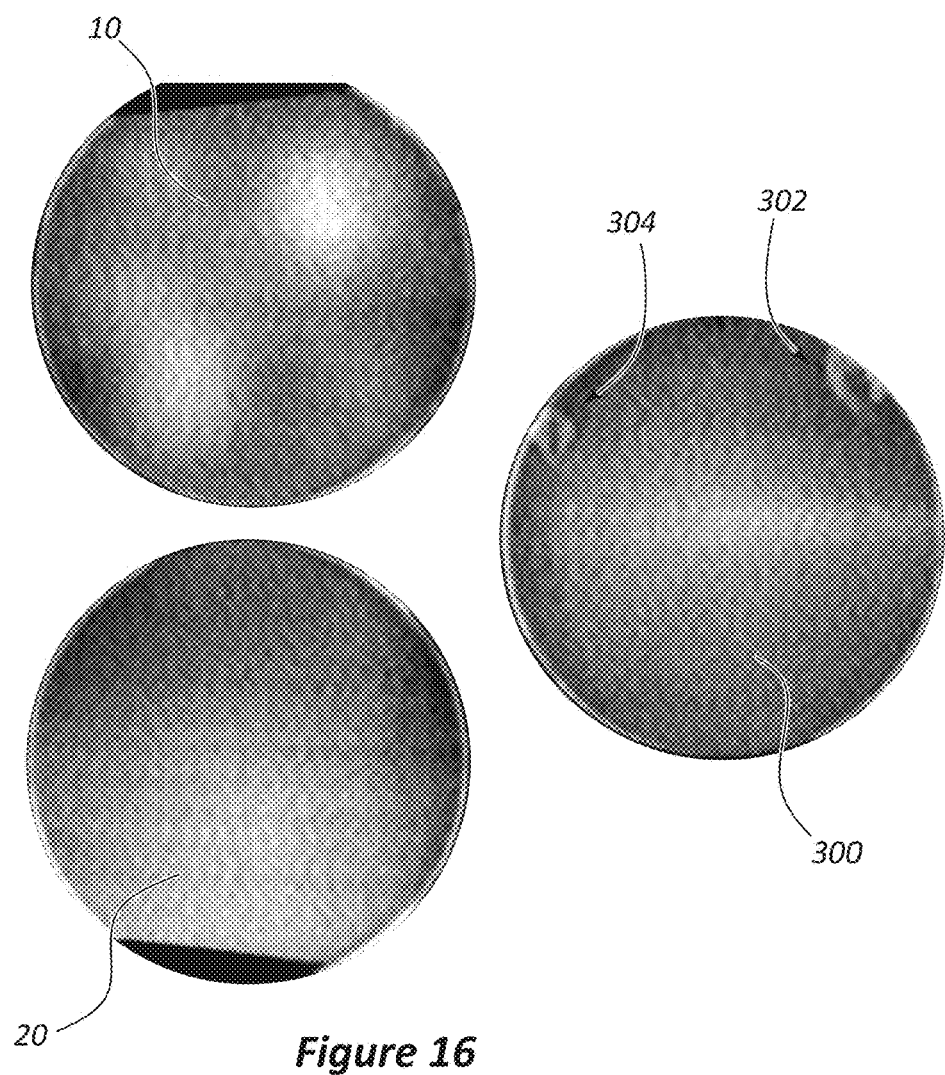
FIG. 16 depicts an X-ray image of a petri dish with microspheres of Example 8.
Figure 17:
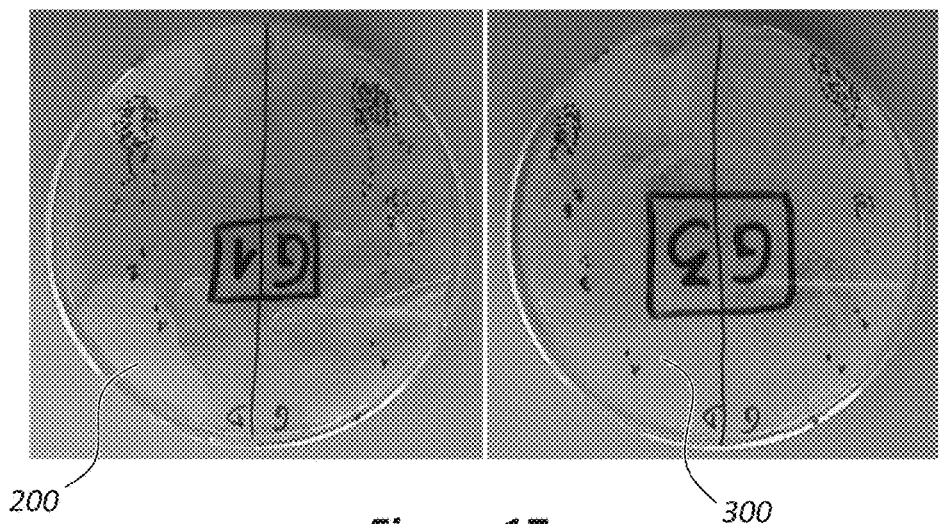
FIG. 17 depicts photographs of the petri dishes of FIGS. 17 and 18 in the same orientation as depicted in the X-ray images.

Samples of exemplary microspheres were tested in X-ray to determine the radiopacity of the microspheres. Microspheres from Examples 7 and 8 (100-300 μm and 300-500 μm from each) were used. Some microspheres of each kind were spread out into gelose (agar) in a Petri dish or a glass tube. A reference was made with Omnipaque 300 (Amersham) diluted in agar (represented by petri dish 10 in FIGS. 15 and 16). A blank was made with only agar (represented by petri dish 20 in FIGS. 15 and 16). A Siemens scanner was used. FIG. 15 depicts the X-ray image of the petri dish 200 with Example 7 microspheres (100-300 μm microspheres represented by the reference numeral 202 and 300-500 μm microspheres represented by the reference numeral 204). FIG. 16 depicts the X-ray image of the petri dish 300 with Example 8 microspheres (100-300 μm microspheres represented by the reference numeral 302 and 300-500 μm microspheres represented by the reference numeral 304). FIG. 17 depicts photographs of the petri dishes 200, 300 in the same orientation as depicted in the X-ray images of FIGS. 15 and 16. The petri dish 200 with Example 7 microspheres is on the left. The petri dish 300 with Example 8 microspheres is on the right. Referring to FIGS. 15 and 16 again, the Omnipaque (300 mg/mL) diluted into the agar (petri dish 10) gave some contrast (large blank spots). There was no contrasted area in the blank sample (petri dish 20). For both exemplary microspheres, the clusters of microspheres were spotted for both sizes.

Example 15

Figure 18:
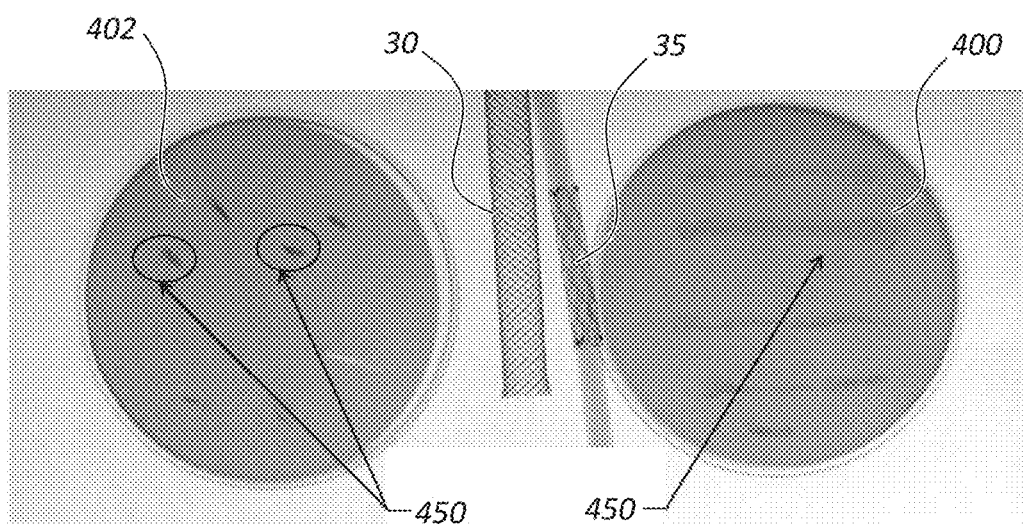
FIG. 18 depicts an X-ray image of petri dishes with microspheres according to certain embodiments compared to metallic stents.

Similar to Example 14, exemplary microspheres 450 were tested in X-ray to compare the radiopacity of the microspheres 450 to metallic stents 30, 35. FIG. 18 depicts an X-ray image of two petri dishes 400, 402 with metallic stents 30, 35 between them. Example 8 microspheres 450 were used in the two petri dishes 400, 402.

Example 16

Samples of exemplary microspheres were tested in vivo. A pig liver, partially-immersed in saline, was embolized using the microspheres of Example 8 with a size range of 100-300 μm. A four French microcatheter with a 0.024" inner diameter that was placed in the vasculature of the liver. The microcather was flushed with saline (0.9% NaCl) to remove all air and then the microspheres were slowly injected until reflux was observed. No contrast agent was used.

Figure 19:
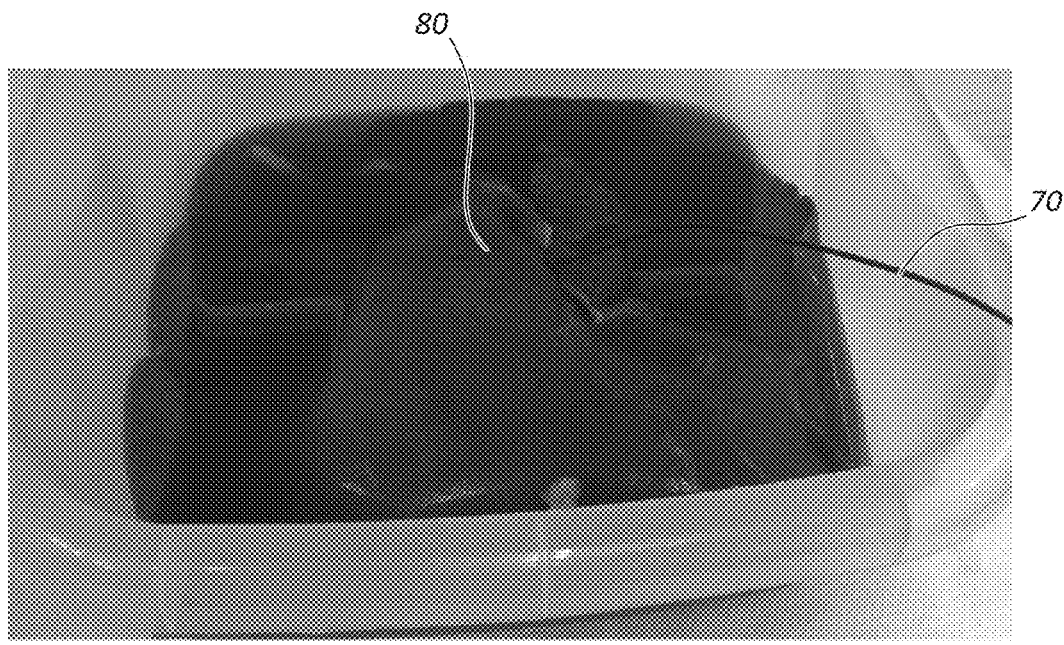
FIG. 19 depicts a picture of a pig liver with a catheter inserted into the vasculature of the liver for delivering microspheres into the vasculature.
Figure 20:
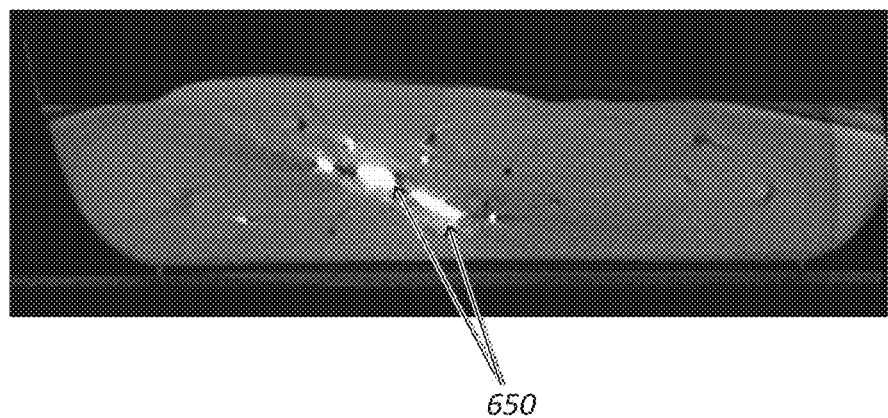
FIG. 20 depicts a CT scan of microspheres of Example 8 in the vasculature of the pig liver of FIG. 19.
Figure 21:
FIG. 21 depicts an X-ray image of the same vasculature and microspheres depicted in FIG. 20.
Figure 22:
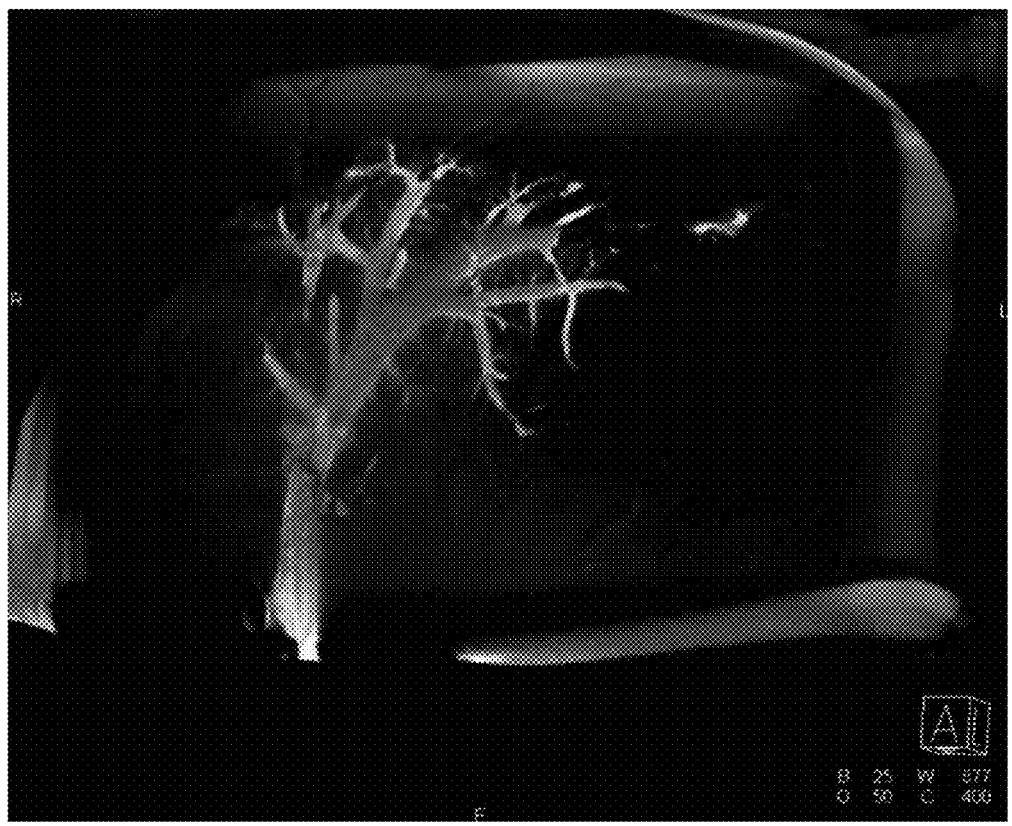
FIG. 22 depicts a three-dimensional reconstitution of the vasculature and microspheres depicted in FIG. 20.

FIG. 19 depicts a picture of the pig liver 80 with the microcatheter 70 inserted into the vasculature of the liver for delivering microspheres into the vasculature. A CT scan (FIG. 20) was conducted and X-ray image (FIG. 21) collected. FIG. 22 depicts a three-dimensional reconstitution of the vasculature and microspheres. FIGS. 20-22 illustrate that the embolized vasculature is full of microspheres 650 and that the microspheres 650 are radiopaque without the presence of a contrast agent. A Siemens Artis zee biplane, VC14 was used for generating the images in FIGS. 20 and 21. A Siemens X-workplace VB15 workstation was used for generating the image depicted in FIG. 22.

Example 17

42 Mole % Monomer Ia/20 Mole % MBA/140 mL Monomers Phase/MRI Agent 25.94 g of Monomer Ia were dissolved in 80 mL of acetate buffer solution at 24° C. (1.4 M NaCl, 0.3 M sodium acetate trihydrate in water, pH adjusted at 6 with acetic acid). The total solution was filtered.

5.57 g of Trisacryl (N-[Tris(hydroxymethyl)methyl] acrylamide, CAS 13880-05-2) and 2.48 g of MBA were dissolved in 60 mL of the same acetate buffer solution at 60° C., and the solution was filtered.

The two solutions were mixed and stirred at room temperature for a few minutes.

3.48 g of Ferucarbotran solution, a superparamagnetic iron oxide contrast agent, (corresponding to 174 mg of Fe (iron)) was added at room temperature to the mixture of monomers and stirred for a few minutes to obtain a homogenous mixture.

The initiator was added (0.34 g of ammonium persulfate) and the monomer solution was poured quickly into 1 L of paraffin oil containing 1.0 g of Arlacel 83 and 1 mL of TEMED at 60° C. under mechanic stirring at 200 rpm.

Figure 23:
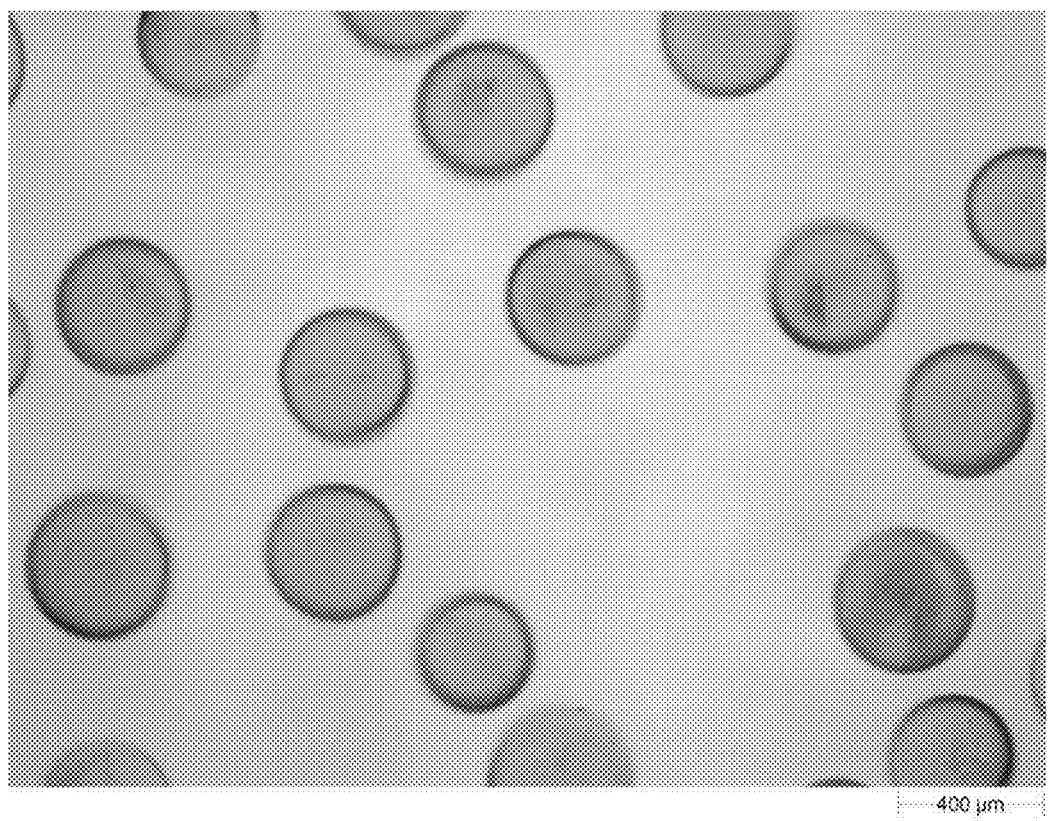
FIG. 23 is a micrograph of 300-500 micron diameter microspheres produced in Example 17, according to one embodiment.

After 55 minutes the polymerization reaction was stopped and the microspheres were washed extensively with water and saline solution (0.9% NaCl). FIG. 23 illustrates the microspheres produced in Example 17 with diameters of about 300-500 microns.

Example 18

Figure 24:
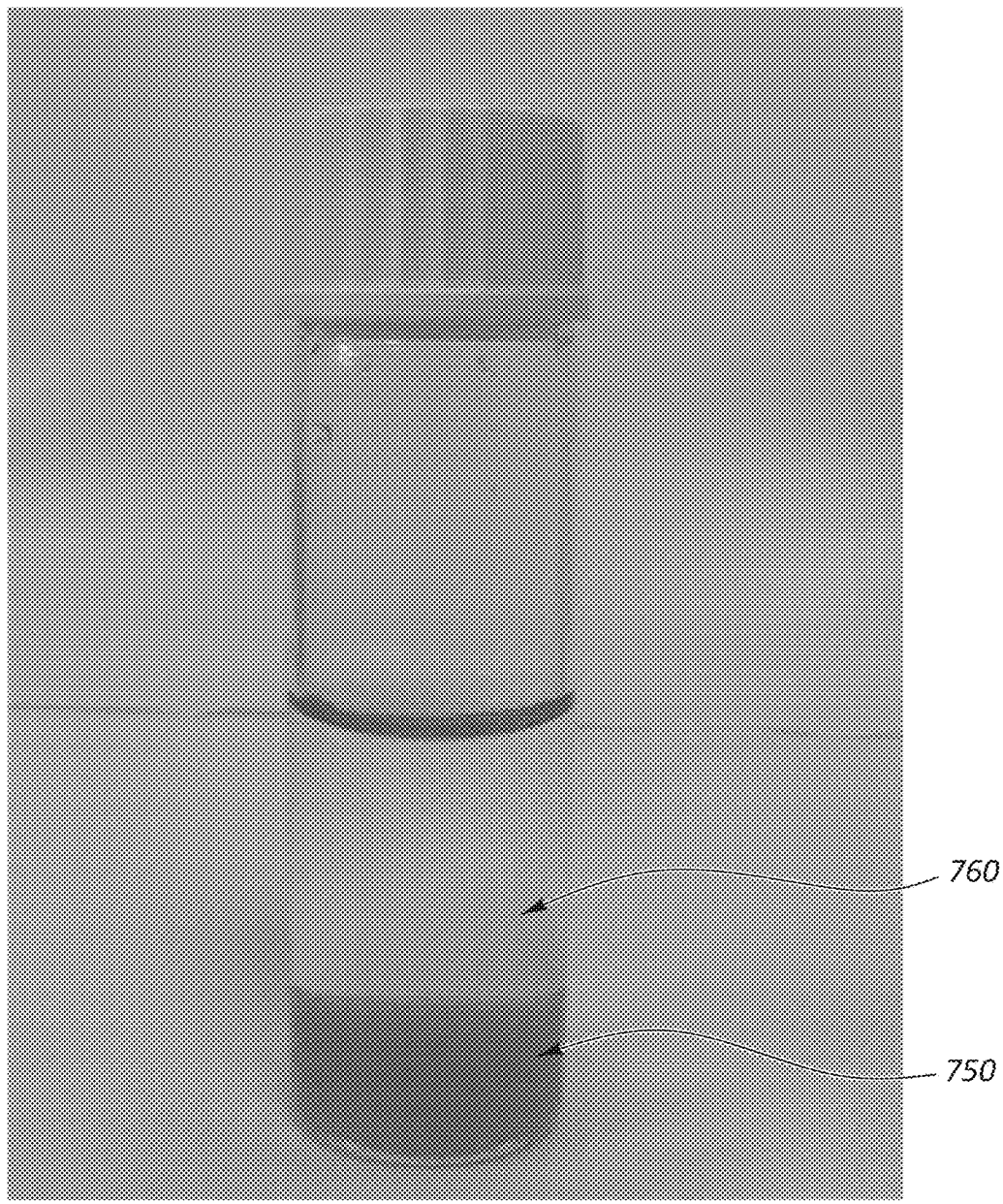
FIGS. 24-25 depict pictures of microspheres of Example 17 settled to the bottom of a vial filled with saline.
Figure 25:
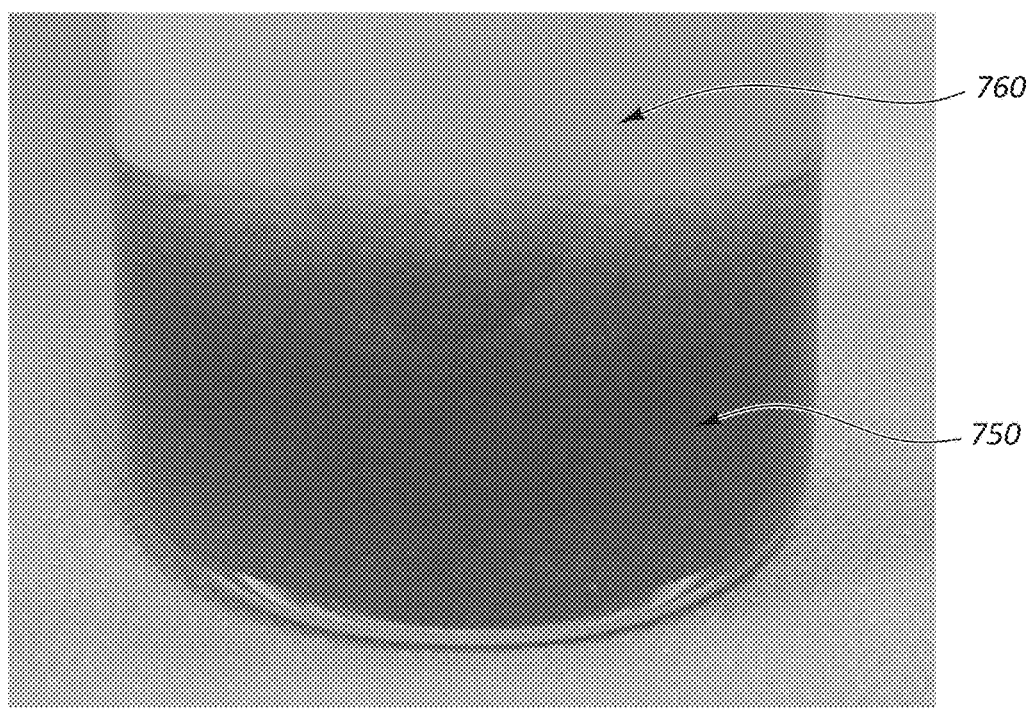

A vial was partially filled with saline 760 and the microspheres 750 of Example 17. FIGS. 24 and 25 depict pictures of microspheres 750 of Example 17 settled to the bottom of a vial filled with saline 760, illustrating that the settled microspheres 750 have incorporated the Ferucarbotran solution.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A microsphere comprising a polymer, wherein the polymer comprises a polymerized monomer of Formula I:

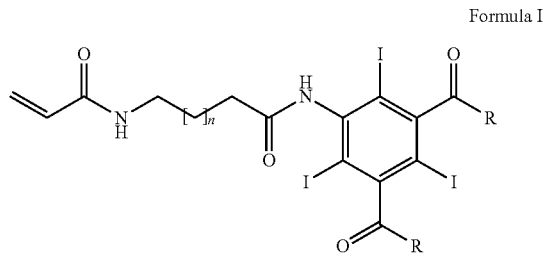

Formula I wherein n is 0-12 and wherein R is either an oxygen-containing moiety or a nitrogen-containing moiety,
wherein the polymer further comprises at least one of a polymerized N-[Tris(hydroxymethyl)methyl] acrylamide, a polymerized diethyl aminoethyl acrylamide, or a polymerized triethyl aminoethyl acrylamide.

2. The microsphere of claim 1, wherein the polymer comprises a polymerized N-[Tris(hydroxymethyl)methyl] acrylamide.

3. The microsphere of claim 1, wherein the polymer comprises a polymerized monomer of Formula Ia or Formula Ib:

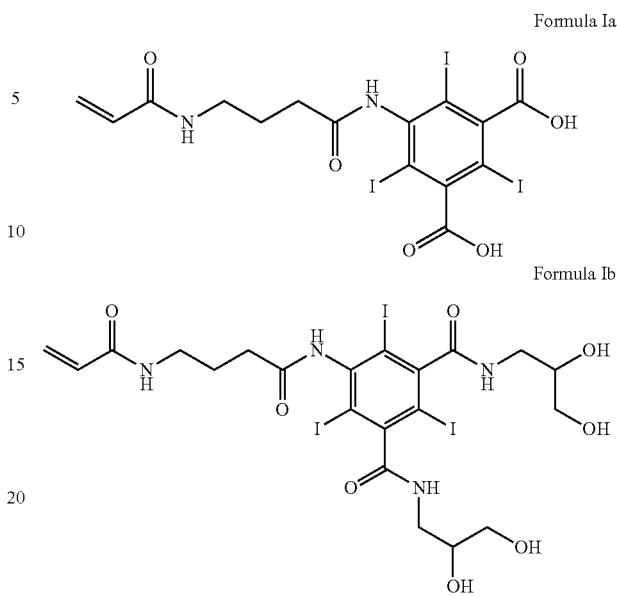

Formula Ia

Formula Ib or a salt thereof.

4. The microsphere of claim 1, wherein the microsphere has a diameter of about 10 microns to about 2000 microns.

5. The microsphere of claim 1, wherein the microsphere swells upon exposure to physiologic conditions.

6. The microsphere of claim 1, wherein the microsphere comprises a therapeutic agent.

7. A method of embolization, the method comprising injecting the microsphere of claim 1 into a blood vessel of a patient.

8. A method of tracking a microsphere in a patient, the method comprising:
introducing the microsphere of claim 1 into a patient; and
imaging at least a portion of the patient and determining a location of the microsphere.

9. The method of claim 8, wherein a contrast agent is not present in the location of the microsphere at the time of imaging.

10. The method of claim 8, further comprising detecting a location of the microsphere more than about 24 hours, more than about 48 hours, more than about a week, or more than about a month after introducing the microsphere.

11. The method of claim 8, further comprising injecting a contrast agent prior to introducing the microsphere to determine an arterial structure of the patient and then after introducing the microsphere, detecting a location of the microsphere after the contrast agent has dissipated.

12. A method of treating a disease, disorder, or cosmetic need of a patient, the method comprising injecting the microsphere of claim 1 into a blood vessel or tissue of the patient.

13. A method of treating cancer, the method comprising injecting the microsphere of claim 1 into a blood vessel of a patient and tracking a location of the microsphere.

14. The microsphere of claim 1, wherein the polymer further comprises at least one of a cross-linker, a gelatin, or a coloring agent.

15. The microsphere of claim 1, wherein the polymer further comprises an additional radiopaque agent.

16. The microsphere of claim 1, wherein the polymer further comprises a magnetic agent.

17. A microsphere comprising a polymer, wherein the polymer comprises a polymerized monomer of Formula I:

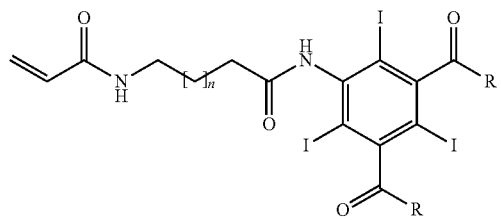

Formula I wherein n is 0-12 and wherein R is either an oxygen-containing moiety or a nitrogen-containing moiety, wherein the polymer further comprises a polymerized N-[Tris(hydroxymethyl) methyl] acrylamide, and wherein the microsphere is non-resorbable within a patient's body.

18. The microsphere of claim 17, wherein the polymer comprises a polymerized monomer of Formula Ia or Formula Ib:

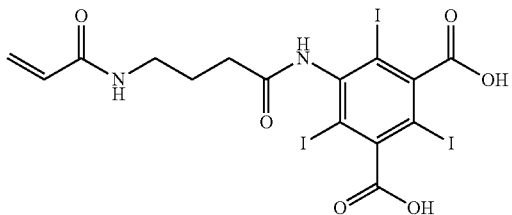

Formula Ia

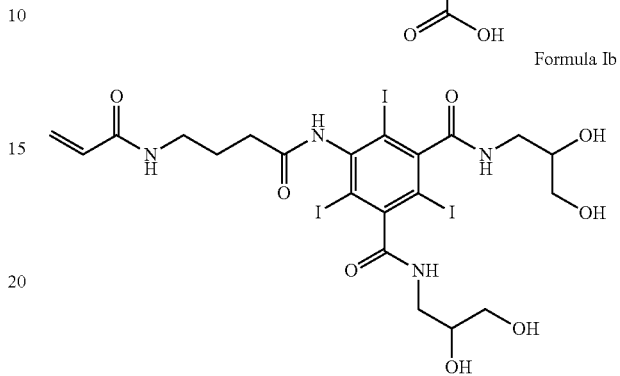

Formula Ib or a salt thereof.

19. The microsphere of claim 17, wherein the microsphere swells upon exposure to physiologic conditions.

20. The microsphere of claim 17, wherein the microsphere comprises a therapeutic agent.

* * * * *